United States Patent
Jonckheere et al.

(10) Patent No.: US 11,771,358 B2
(45) Date of Patent: Oct. 3, 2023

(54) RHYTHMIC SYNCHRONIZATION OF MOTOR NEURON DISCHARGES AND THEIR BURST RATE VARIABILITY

(71) Applicant: UNIVERSITY OF SOUTHERN CALIFORNIA, Los Angeles, CA (US)

(72) Inventors: Edmond A. Jonckheere, Los Angeles, CA (US); Roberto Martin Del Campo Vera, Los Angeles, CA (US)

(73) Assignee: UNIVERSITY OF SOUTHERN CALIFORNIA, Los Angeles, CA (US)

(*) Notice: Subject to any disclaimer, the term of this patent is extended or adjusted under 35 U.S.C. 154(b) by 300 days.

(21) Appl. No.: 16/772,675

(22) PCT Filed: Dec. 20, 2018

(86) PCT No.: PCT/US2018/066781
§ 371 (c)(1),
(2) Date: Jun. 12, 2020

(87) PCT Pub. No.: WO2019/126490
PCT Pub. Date: Jun. 27, 2019

(65) Prior Publication Data
US 2020/0305743 A1   Oct. 1, 2020

Related U.S. Application Data

(60) Provisional application No. 62/608,474, filed on Dec. 20, 2017.

(51) Int. Cl.
*A61B 5/00*   (2006.01)
*A61B 5/24*   (2021.01)
(Continued)

(52) U.S. Cl.
CPC ............. *A61B 5/24* (2021.01); *A61B 5/318* (2021.01); *A61B 5/369* (2021.01); *A61B 5/389* (2021.01);
(Continued)

(58) Field of Classification Search
CPC ......... A61B 5/726; A61B 5/35; A61B 5/7264; A61B 5/7203; A61B 5/7257; A61B 5/24;
(Continued)

(56) References Cited

U.S. PATENT DOCUMENTS 4,603,703 A * 8/1986 McGill .................... A61B 5/35
                                                                 600/546
6,366,805 B1 * 4/2002 Lutz ...................... A61B 5/0006
                                                                 600/544
(Continued)

OTHER PUBLICATIONS

International Search Report and Written Opinion of the International Searching Authority (dated Apr. 9, 2019) for Corresponding International PCT Patent Application No. PCT/US18/066781, filed Dec. 20, 2018.

*Primary Examiner* — Rex R Holmes
*Assistant Examiner* — Sana Sahand
(74) *Attorney, Agent, or Firm* — SNELL & WILMER L.L.P.

(57) ABSTRACT

Methods, systems, and apparatus for detecting rhythmic synchronization of motor neurons. The system includes one or more sensors for receiving a first signal that measures an electrical signal of one or more neurons, the first signal having a first plurality of specific bursts. The system includes a processor connected to the one or more sensors. The processor is configured to receive the first signal. The processor is configured to generate a second signal based on the first signal using a discrete wavelet transform, the second signal having a second plurality of specific bursts. The processor is configured to determine a time delay between a
(Continued)

specific burst within the first plurality of specific bursts and a specific burst within the second plurality of specific bursts using one or more expert rules. The processor is configured to apply the time delay to the first signal.

14 Claims, 26 Drawing Sheets

(51) Int. Cl.
*A61B 5/318* (2021.01)
*A61B 5/369* (2021.01)
*A61B 5/389* (2021.01)

(52) U.S. Cl.
CPC ............ *A61B 5/726* (2013.01); *A61B 5/7278* (2013.01); *A61B 5/742* (2013.01); *A61B 5/4082* (2013.01); *A61B 5/4094* (2013.01); *A61B 5/4356* (2013.01)

(58) Field of Classification Search
CPC ......... A61B 5/318; A61B 5/369; A61B 5/389; A61B 5/7278; A61B 5/742; A61B 5/4082; A61B 5/4094; A61B 5/4356; A61B 5/352; A61B 5/316; A61B 5/1101
See application file for complete search history.

(56) References Cited

U.S. PATENT DOCUMENTS

| | | | |
|---|---|---|---|
| 8,244,475 B2 | 8/2012 | Aguilar et al. | |
| 8,315,970 B2 | 11/2012 | Zalay et al. | |
| 8,750,971 B2 | 6/2014 | Tran | |
| 2003/0171685 A1* | 9/2003 | Lesser | A61F 7/12 600/509 |
| 2006/0015034 A1* | 1/2006 | Martinerie | A61B 5/369 600/544 |
| 2008/0294063 A1* | 11/2008 | Bibian | A61B 5/4035 600/544 |
| 2012/0310051 A1* | 12/2012 | Addison | A61B 5/02416 600/323 |
| 2014/0198888 A1* | 7/2014 | Chalamala | G06F 17/148 375/354 |

* cited by examiner

| Type of Subject | Subject # | Signal | Sample Size[a] | Mean[b] Experimental | Mean[b] Theoretical | %error | Standard Deviation[b] Experimental | Standard Deviation[b] Theoretical | %error | Best Fit[c] | Fitted Parameter Estimates Type | Fitted Parameter Estimates Parameter | Fitted Parameter Estimates Estimate | Goodness of Fit Test[d] p-value |
|---|---|---|---|---|---|---|---|---|---|---|---|---|---|---|
| Quad | 1 | Lumbar | 131 | 0.83679 | 0.83671 | 0.00956 | 0.09978 | 0.10269 | 2.83377 | Weibull | Scale | α | 0.8802891 | 0.25 |
| | | | | | | | | | | | Shape | β | 9.7908324 | |
| | 2 | Thoracic | 60 | 0.98695 | 0.98959 | 0.26678 | 0.16850 | 0.15875 | 6.14173 | Weibull | Scale | α | 1.0551864 | 0.1975 |
| | | | | | | | | | | | Shape | β | 7.3575348 | |
| | 3 | Cervical | 297 | 0.79074 | 0.79074 | 0.00073 | 0.07175 | 0.06955 | 3.16109 | Normal 2 Mixture | Location | $\mu_1$ | 0.7582432 | 0.4727 |
| | | | | | | | | | | | Location | $\mu_2$ | 0.7990039 | |
| | | | | | | | | | | | Dispersion | $\sigma_1$ | 0.1110593 | |
| | | | | | | | | | | | Dispersion | $\sigma_2$ | 0.0509513 | |
| | | | | | | | | | | | Probability | $\pi_1$ | 0.2026008 | |
| | | | | | | | | | | | Probability | $\pi_2$ | 0.7973992 | |
| Control | | Thoracic | 142 | 0.80970 | 0.80969 | 0.00119 | 0.05908 | 0.05819 | 1.52254 | Normal 3 Mixture | Location | $\mu_1$ | 0.7433704 | 0.4605 |
| | | | | | | | | | | | Location | $\mu_2$ | 0.8374764 | |
| | | | | | | | | | | | Location | $\mu_2$ | 1.0203324 | |
| | | | | | | | | | | | Dispersion | $\sigma_1$ | 0.0261000 | |
| | | | | | | | | | | | Dispersion | $\sigma_2$ | 0.0302071 | |
| | | | | | | | | | | | Dispersion | $\sigma_3$ | 0.0200882 | |
| | | | | | | | | | | | Probability | $\pi_1$ | 0.3226223 | |
| | | | | | | | | | | | Probability | $\pi_2$ | 0.6632976 | |
| | | | | | | | | | | | Probability | $\pi_3$ | 0.0140801 | |

FROM FIG. 9A

| Type of Subject | Subject # | Signal | Sample Size[a] | Mean[b] | | | Standard Deviation[b] | | | Best Fit[c] | Fitted Parameter Estimates | | | Goodness of Fit Test[d] p-value |
|---|---|---|---|---|---|---|---|---|---|---|---|---|---|---|
| | | | | Experimental | Theoretical | %error | Experimental | Theoretical | %error | | Type | Parameter | Estimate | |
| Control | 3 | Lumbar | 183 | 0.68051 | 0.68050 | 0.00090 | 0.08635 | 0.08508 | 1.49601 | Normal 3 Mixture | Location | μ1 | 0.4872577 | 0.4652 |
| | | | | | | | | | | | Location | μ2 | 0.6821022 | |
| | | | | | | | | | | | Location | μ3 | 0.9507306 | |
| | | | | | | | | | | | Dispersion | σ1 | 0.0116068 | |
| | | | | | | | | | | | Dispersion | σ2 | 0.0720919 | |
| | | | | | | | | | | | Dispersion | σ3 | 0.0171289 | |
| | | | | | | | | | | | Probability | π1 | 0.0299150 | |
| | | | | | | | | | | | Probability | π2 | 0.9543367 | |
| | | | | | | | | | | | Probability | π3 | 0.0157483 | |
| | | Sacral | 257 | 0.71217 | 0.71215 | 0.00245 | 0.09731 | 0.09614 | 1.21324 | Normal 2 Mixture | Location | μ1 | 0.7089559 | 0.4707 |
| | | | | | | | | | | | Location | μ2 | 1.1198451 | |
| | | | | | | | | | | | Dispersion | σ1 | 0.0894392 | |
| | | | | | | | | | | | Dispersion | σ2 | 0.0236820 | |
| | | | | | | | | | | | Probability | π1 | 0.9922274 | |
| | | | | | | | | | | | Probability | π2 | 0.0077726 | |

FROM FIG. 9B

| Type of Subject | Subject # | Signal | Sample Size[a] | Mean[b] | | | Standard Deviation[b] | | | Best Fit[c] | Fitted Parameter Estimates | | | Goodness of Fit Test[d] p-value |
|---|---|---|---|---|---|---|---|---|---|---|---|---|---|---|
| | | | | Experimental | Theoretical | %error | Experimental | Theoretical | %error | | Type | Parameter | Estimate | |
| Control | 4 | Cervical | 1,055 | 0.69755 | 0.69756 | 0.00088 | 0.04814 | 0.04753 | 1.28368 | Normal 3 Mixture | Location | μ1 | 0.5211892 | 0.4855 |
| | | | | | | | | | | | Location | μ2 | 0.7008101 | |
| | | | | | | | | | | | Location | μ3 | 0.6990413 | |
| | | | | | | | | | | | Dispersion | σ1 | 0.0106487 | |
| | | | | | | | | | | | Dispersion | σ2 | 0.0186435 | |
| | | | | | | | | | | | Dispersion | σ3 | 0.0974058 | |
| | | | | | | | | | | | Probability | π1 | 0.0166192 | |
| | | | | | | | | | | | Probability | π2 | 0.8313767 | |
| | | | | | | | | | | | Probability | π3 | 0.1520042 | |
| | | Thoracic | 1,550 | 0.69693 | 0.69693 | 0.00001 | 0.02918 | 0.02857 | 2.12082 | Normal 3 Mixture | Location | μ1 | 0.6663625 | 0.4881 |
| | | | | | | | | | | | Location | μ2 | 0.6998140 | |
| | | | | | | | | | | | Location | μ3 | 0.6913961 | |
| | | | | | | | | | | | Dispersion | σ1 | 0.0868998 | |
| | | | | | | | | | | | Dispersion | σ2 | 0.0165026 | |
| | | | | | | | | | | | Dispersion | σ3 | 0.0331125 | |
| | | | | | | | | | | | Probability | π1 | 0.0507722 | |
| | | | | | | | | | | | Probability | π2 | 0.8083748 | |
| | | | | | | | | | | | Probability | π3 | 0.1408530 | |

FIG. 9C

| Type of Subject | Subj. # | Signal | Sample Size[a] | Mean[b] Experimental | Mean[b] Theoretical | %error | Standard Deviation[b] Experimental | Standard Deviation[b] Theoretical | %error | Best Fit[c] | Fitted Parameter Estimates Type | Fitted Parameter Estimates Parameter | Fitted Parameter Estimates Estimate | Goodness of Fit Test[d] p-value |
|---|---|---|---|---|---|---|---|---|---|---|---|---|---|---|
| Control | 4 | Lumbar | 544 | 0.69361 | 0.69361 | 0.00050 | 0.03051 | 0.03020 | 1.01183 | Normal 3 Mixture | Location | $\mu_1$ | 0.5177513 | 0.4758 |
| | | | | | | | | | | | Location | $\mu_2$ | 0.6904178 | |
| | | | | | | | | | | | Location | $\mu_3$ | 0.7026590 | |
| | | | | | | | | | | | Dispersion | $\sigma_1$ | 0.0077241 | |
| | | | | | | | | | | | Dispersion | $\sigma_2$ | 0.0128245 | |
| | | | | | | | | | | | Dispersion | $\sigma_3$ | 0.0356578 | |
| | | | | | | | | | | | Probability | $\pi_1$ | 0.0091908 | |
| | | | | | | | | | | | Probability | $\pi_2$ | 0.6063979 | |
| | | | | | | | | | | | Probability | $\pi_3$ | 0.3844114 | |
| | | Sacral | 265 | 0.71434 | 0.71434 | 0.00057 | 0.06640 | 0.06549 | 1.39002 | Normal 3 Mixture | Location | $\mu_1$ | 0.5062527 | 0.4711 |
| | | | | | | | | | | | Location | $\mu_2$ | 0.6927545 | |
| | | | | | | | | | | | Location | $\mu_3$ | 0.7269021 | |
| | | | | | | | | | | | Dispersion | $\sigma_1$ | 0.0228341 | |
| | | | | | | | | | | | Dispersion | $\sigma_2$ | 0.0117517 | |
| | | | | | | | | | | | Dispersion | $\sigma_3$ | 0.0635254 | |
| | | | | | | | | | | | Probability | $\pi_1$ | 0.0223802 | |
| | | | | | | | | | | | Probability | $\pi_2$ | 0.2231447 | |
| | | | | | | | | | | | Probability | $\pi_3$ | 0.7544751 | |

FROM FIG. 10A

| Type of Subject | Subj. # | Signal | Sample Size[a] | Mean[b] | | | Standard Deviation[b] | | | Best Fit[c] | Fitted Parameter Estimates | | | Goodness of Fit Test[d] p-value |
|---|---|---|---|---|---|---|---|---|---|---|---|---|---|---|
| | | | | Experimental | Theoretical | %error | Experimental | Theoretical | %error | | Type | Parameter | Estimate | |
| Control | 5 | Cervical | 179 | 0.88047 | 0.88045 | 0.00200 | 0.19756 | 0.19505 | 1.28573 | Normal 3 Mixture | Location | $\mu_1$ | 0.5437492 | 0.4648 |
| | | | | | | | | | | | Location | $\mu_2$ | 0.8985177 | |
| | | | | | | | | | | | Location | $\mu_3$ | 1.6026796 | |
| | | | | | | | | | | | Dispersion | $\sigma_1$ | 0.0343333 | |
| | | | | | | | | | | | Dispersion | $\sigma_2$ | 0.1466987 | |
| | | | | | | | | | | | Dispersion | $\sigma_3$ | 0.0351786 | |
| | | | | | | | | | | | Probability | $\pi_1$ | 0.0841804 | |
| | | | | | | | | | | | Probability | $\pi_2$ | 0.8990634 | |
| | | | | | | | | | | | Probability | $\pi_3$ | 0.0167563 | |
| | | Lumbar | 199 | 0.96771 | 0.96771 | 0.00049 | 0.20595 | 0.19590 | 5.12965 | Normal 2 Mixture | Location | $\mu_1$ | 0.9999384 | 0.4667 |
| | | | | | | | | | | | Location | $\mu_2$ | 0.9611284 | |
| | | | | | | | | | | | Dispersion | $\sigma_1$ | 0.3388004 | |
| | | | | | | | | | | | Dispersion | $\sigma_2$ | 0.1248396 | |
| | | | | | | | | | | | Probability | $\pi_1$ | 0.2282849 | |
| | | | | | | | | | | | Probability | $\pi_2$ | 0.7717151 | |
| | | Sacral | 361 | 1.00026 | 1.00025 | 0.00064 | 0.24514 | 0.24297 | 0.89479 | Normal 2 Mixture | Location | $\mu_1$ | 0.9255663 | 0.4753 |
| | | | | | | | | | | | Location | $\mu_2$ | 1.4218577 | |
| | | | | | | | | | | | Dispersion | $\sigma_1$ | 0.1636967 | |

FROM FIG. 10B

| Type of Subject | Subj. # | Signal | Sample Size | Mean$^b$ Experimental | Mean$^b$ Theoretical | %error | Standard Deviation$^b$ Experimental | Standard Deviation$^b$ Theoretical | %error | Best Fit$^c$ | Fitted Parameter Estimates Type | Parameter | Estimate | Goodness of Fit Test$^d$ p-value |
|---|---|---|---|---|---|---|---|---|---|---|---|---|---|---|
| | | Sacral | 361 | 1.00026 | 1.00025 | 0.00064 | 0.24514 | 0.24297 | 0.89479 | Normal 2 Mixture | Dispersion | $\sigma_2$ | 0.1782215 | 0.4753 |
| | | | | | | | | | | | Probability | $\pi_1$ | 0.8495092 | |
| | | | | | | | | | | | Probability | $\pi_2$ | 0.1504908 | |
| | | Thoracic | 285 | 0.87775 | 0.87776 | 0.00059 | 0.17501 | 0.17362 | 0.79960 | Normal 2 Mixture | Location | $\mu_1$ | 0.6472983 | 0.4721 |
| | | | | | | | | | | | Location | $\mu_2$ | 0.9608497 | |
| | | | | | | | | | | | Dispersion | $\sigma_1$ | 0.0912896 | |
| | | | | | | | | | | | Dispersion | $\sigma_2$ | 0.1093363 | |
| | | | | | | | | | | | Probability | $\pi_1$ | 0.2650080 | |
| | | | | | | | | | | | Probability | $\pi_2$ | 0.7349920 | |
| Control | 6 | Lumbar | 202 | 0.86156 | 0.86156 | 0.00008 | 0.13750 | 0.13609 | 1.03961 | Normal 2 Mixture | Location | $\mu_1$ | 0.7772509 | 0.4669 |
| | | | | | | | | | | | Location | $\mu_2$ | 1.0203541 | |
| | | | | | | | | | | | Dispersion | $\sigma_1$ | 0.0616972 | |
| | | | | | | | | | | | Dispersion | $\sigma_2$ | 0.0873302 | |
| | | | | | | | | | | | Probability | $\pi_1$ | 0.6531933 | |
| | | | | | | | | | | | Probability | $\pi_2$ | 0.3468067 | |
| | | Sacral | 144 | 0.87099 | 0.87099 | 0.00034 | 0.13305 | 0.13092 | 1.62844 | Normal 2 Mixture | Location | $\mu_1$ | 0.7801195 | 0.4608 |
| | | | | | | | | | | | Location | $\mu_2$ | 0.9987842 | |
| | | | | | | | | | | | Dispersion | $\sigma_1$ | 0.0563301 | |
| | | | | | | | | | | | Dispersion | $\sigma_2$ | 0.0940075 | |
| | | | | | | | | | | | Probability | $\pi_1$ | 0.5844435 | |
| | | | | | | | | | | | Probability | $\pi_2$ | 0.4155565 | |

| Type of Subject | Subj. # | Signal | Sample Size[a] | Mean[b] | | | Standard Deviation[b] | | | Best Fit[c] | Fitted Parameter Estimates | | | Goodness of Fit Test[d] p-value |
|---|---|---|---|---|---|---|---|---|---|---|---|---|---|---|
| | | | | Experimental | Theoretical | %error | Experimental | Theoretical | %error | | Type | Parameter | Estimate | |
| Control | 7 | Lumbar | 224 | 0.79185 | 0.79185 | 0.00037 | 0.16560 | 0.16096 | 2.88156 | Normal 2 Mixture | Location | μ1 | 0.7358333 | 0.4686 |
| | | | | | | | | | | | Location | μ2 | 0.9235629 | |
| | | | | | | | | | | | Dispersion | σ1 | 0.0766122 | |
| | | | | | | | | | | | Dispersion | σ2 | 0.2197815 | |
| | | | | | | | | | | | Probability | π1 | 0.7016254 | |
| | | | | | | | | | | | Probability | π2 | 0.2983746 | |
| | | Sacral | 125 | 0.73425 | 0.73424 | 0.00156 | 0.09611 | 0.09418 | 2.05266 | Normal 2 Mixture | Location | μ1 | 0.7148177 | 0.4579 |
| | | | | | | | | | | | Location | μ2 | 0.8971440 | |
| | | | | | | | | | | | Dispersion | σ1 | 0.0795113 | |
| | | | | | | | | | | | Dispersion | σ2 | 0.0231078 | |
| | | | | | | | | | | | Probability | π1 | 0.8934829 | |
| | | | | | | | | | | | Probability | π2 | 0.1065171 | |
| | 8 | Cervical | 183 | 0.83857 | 0.83868 | 0.00104 | 0.14154 | 0.14027 | 0.90740 | Normal 2 Mixture | Location | μ1 | 0.6780456 | 0.4652 |
| | | | | | | | | | | | Location | μ2 | 0.9284455 | |
| | | | | | | | | | | | Dispersion | σ1 | 0.0476830 | |
| | | | | | | | | | | | Dispersion | σ2 | 0.0831964 | |
| | | | | | | | | | | | Probability | π1 | 0.3584937 | |
| | | | | | | | | | | | Probability | π2 | 0.6415063 | |

FROM FIG. 11A

| Type of Subject | Subj. # | Signal | Sample Size[a] | Mean[b] Experimental | Mean[b] Theoretical | %error | Standard Deviation[b] Experimental | Standard Deviation[b] Theoretical | %error | Best Fit[c] | Fitted Parameter Estimates Type | Fitted Parameter Estimates Parameter | Fitted Parameter Estimates Estimate | Goodness of Fit Test[d] p-value |
|---|---|---|---|---|---|---|---|---|---|---|---|---|---|---|
| Control | 8 | Thoracic | 222 | 0.85704 | 0.85704 | 0.00032 | 0.13054 | 0.12937 | 0.90700 | Normal 2 Mixture | Location | $\mu_1$ | 0.7333043 | 0.4684 |
| | | | | | | | | | | | Location | $\mu_2$ | 0.9528567 | |
| | | | | | | | | | | | Dispersion | $\sigma_1$ | 0.0714954 | |
| | | | | | | | | | | | Dispersion | $\sigma_2$ | 0.0685575 | |
| | | | | | | | | | | | Probability | $\pi_1$ | 0.4364308 | |
| | | | | | | | | | | | Probability | $\pi_2$ | 0.5635692 | |
| | | Lumbar | 339 | 0.77250 | 0.77259 | 0.00071 | 0.12678 | 0.12602 | 0.60054 | Normal 2 Mixture | Location | $\mu_1$ | 0.7135704 | 0.4745 |
| | | | | | | | | | | | Location | $\mu_2$ | 0.9533303 | |
| | | | | | | | | | | | Dispersion | $\sigma_1$ | 0.0753422 | |
| | | | | | | | | | | | Dispersion | $\sigma_2$ | 0.0616300 | |
| | | | | | | | | | | | Probability | $\pi_1$ | 0.7538200 | |
| | | | | | | | | | | | Probability | $\pi_2$ | 0.2461800 | |
| | | Sacral | 146 | 0.83955 | 0.83956 | 0.00106 | 0.13539 | 0.13373 | 1.24495 | Normal 3 Mixture | Location | $\mu_1$ | 0.7022492 | 0.4611 |
| | | | | | | | | | | | Location | $\mu_2$ | 0.7743037 | |
| | | | | | | | | | | | Location | $\mu_3$ | 0.9565582 | |
| | | | | | | | | | | | Dispersion | $\sigma_1$ | 0.0689697 | |
| | | | | | | | | | | | Dispersion | $\sigma_2$ | 0.0171418 | |

FROM FIG. 11B

| Type of Subject | Subj. # | Signal | Sample Size[a] | Mean[b] | | | Standard Deviation[b] | | | Best Fit[c] | Fitted Parameter Estimates | | | Goodness of Fit Test[d] p-value |
|---|---|---|---|---|---|---|---|---|---|---|---|---|---|---|
| | | | | Experimental | Theoretical | %error | Experimental | Theoretical | %error | | Type | Parameter | Estimate | |
| Control | 9 | Thoracic | 334 | 0.83843 | 0.83843 | 0.00020 | 0.10321 | 0.10253 | 0.66353 | Normal 2 Mixture | Location | $\mu_1$ | 0.7648442 | 0.4743 |
| | | | | | | | | | | | Location | $\mu_2$ | 0.9331420 | |
| | | | | | | | | | | | Dispersion | $\sigma_1$ | 0.0649377 | |
| | | | | | | | | | | | Dispersion | $\sigma_2$ | 0.0517103 | |
| | | | | | | | | | | | Probability | $\pi_1$ | 0.5627745 | |
| | | | | | | | | | | | Probability | $\pi_2$ | 0.4372255 | |
| | | Lumbar | 307 | 0.83850 | 0.83849 | 0.00773 | 0.10641 | 0.10565 | 0.71589 | Normal 2 Mixture | Location | $\mu_1$ | 0.7694800 | 0.4732 |
| | | | | | | | | | | | Location | $\mu_2$ | 0.9435923 | |
| | | | | | | | | | | | Dispersion | $\sigma_1$ | 0.0710122 | |
| | | | | | | | | | | | Dispersion | $\sigma_2$ | 0.0467439 | |
| | | | | | | | | | | | Probability | $\pi_1$ | 0.6036399 | |
| | | | | | | | | | | | Probability | $\pi_2$ | 0.3963601 | |

FIG. 11C

RHYTHMIC SYNCHRONIZATION OF MOTOR NEURON DISCHARGES AND THEIR BURST RATE VARIABILITY

CROSS-REFERENCE TO RELATED APPLICATIONS

This application claims priority to and the benefit of U.S. Provisional Patent Application No. 62/608,474 titled "RHYTHMIC SYNCHRONIZATION OF MOTOR NEURON DISCHARGES AND THEIR BURST RATE VARIABILITY," filed on Dec. 20, 2017, and the entirety of which is hereby incorporated by reference herein.

BACKGROUND

Field

This specification relates to a system, a method or an apparatus for detecting rhythmic synchronization of motor neurons.

Description of the Related Art

The Discrete Wavelet Transform (DWT) has long been used to explain motor unit recruitment by selecting a mother wavelet similar to the Motor Units Actions Potentials (MUAPs), such as Daubechies 3 (db3). High scale subbands have served to single out the spiking neuronal events and lower scale subbands are mainly comprised of high-frequency noise. However, the periodicity of the DWT and variability in the return times of bursts may cause the multiple MUAPs to be misaligned with the mother wavelet during the spiking events.

Accordingly, there is a need for a system that delays the DWT multiple times and increases the waveform matching between a raw signal, such as a surface electromyographic (sEMG) signal, and its sub-signal, such as an 8-level sub-signal, to provide time-localization and characterization of spiking events.

SUMMARY

In general, one aspect of the subject matter described in this specification may be embodied in a system for detecting rhythmic synchronization of motor neurons. The system includes one or more sensors for receiving a first signal that measures an electrical signal of one or more neurons, the first signal having a first plurality of specific bursts. The system includes a processor connected to the one or more sensors. The processor is configured to receive the first signal. The processor is configured to generate a second signal based on the first signal using a discrete wavelet transform, the second signal having a second plurality of specific bursts. The processor is configured to determine a time delay between a specific burst within the first plurality of specific bursts and a specific burst within the second plurality of specific bursts using one or more expert rules. The processor is configured to apply the time delay to the first signal.

These and other embodiments may optionally include one or more of the following features. The system may include an amplifier to amplify the first signal prior to inputting into the processor. The system may include an analog-to-digital converter (ADC) to sample the first signal and convert the first signal into a digital signal for input into the processor. The system may include a display for rendering an image that displays the first signal and the second signal. The system may include a memory for storing instructions for the processor to execute, the instructions including the discrete wavelet transform and the one or more expert rules.

The time delay may be based on one or more predetermined time delays. The time delay may correspond to a minimal error between the first specific burst and the second specific burst. The first signal may include a first plurality of peaks, a first plurality of valleys, and a first plurality of slopes between each of the peaks and valleys, the first plurality of specific bursts being the first plurality of peaks. The second signal may include a second plurality of peaks, a second plurality of valleys, and a second plurality of slopes between each of the peaks and valleys, the second plurality of specific bursts being the second plurality of peaks. Determining the time shift may include comparing at least one peak within the first plurality of peaks, at least one valley within the first plurality of valleys, or at least one slope within the first plurality of slopes to at least one peak within the second plurality of peaks, at least one valley within the second plurality of valleys, or at least one slope within the second plurality of slopes.

The first signal may be a raw signal of an electromyographic (sEMG) signal, wherein the discrete wavelet transform is a doublet waveform that is in a D8 subband of the Daubechies 3 (db3) wavelet decomposition of the sEMG signal. The first signal may be a raw signal of at least one of an electromyogram, an electroencephalogram, or an electrocardiogram. The one or more sensors include one or more electrodes that are positioned on paraspinal muscles of a human.

The processor may be configured to generate a new second signal having an adjusted second plurality of specific bursts using the discrete wavelet transform, the new second signal being based on the first signal and the applied time delay. The processor may be configured to determine a second time delay between a second specific burst within the first plurality of specific bursts and a second specific burst within the adjusted second plurality of specific bursts using the one or more expert rules. The processor may be configured to apply the second time delay to the first signal.

In another aspect, the subject matter may be embodied in a method for detecting rhythmic synchronization of motor neurons. The method includes receiving, by a processor, a first signal having a first plurality of specific bursts. The method includes generating, by the processor, a second signal based on the first signal using a discrete wavelet transform, the second signal having a second plurality of specific bursts. The method includes determining, by the processor, a time delay between a specific burst within the first plurality of specific bursts and a specific burst within the second plurality of specific bursts using one or more expert rules. The method includes applying, by the processor, the time delay to the first signal.

BRIEF DESCRIPTION OF THE DRAWINGS

Other systems, methods, features, and advantages of the present invention will be apparent to one skilled in the art upon examination of the following figures and detailed description. Component parts shown in the drawings are not necessarily to scale, and may be exaggerated to better illustrate the important features of the present invention.

FIG. 9A-9C illustrate part 1 of 3 of a distribution analysis according to an aspect of the invention.

FIG. 10A-10C illustrate part 2 of 3 of a distribution analysis according to an aspect of the invention.

FIG. 11A-11C illustrate part 3 of 3 of a distribution analysis according to an aspect of the invention.

DETAILED DESCRIPTION

Disclosed herein are systems, apparatuses, devices and/or methods for detecting rhythmic synchronization of motor neurons.

Under some conditions, the surface electromyographic (sEMG) activity recorded along the paraspinal muscles of a subject may show some standing wave properties (oscillations), even though the trunk (torso) of the subject does not manifest a visually obvious movement. These conditions can be reproduced by putting the subject in the prone position and applying light pressure at some specific "gateway" points of the spine (usually the neck and the coccyx) to elicit the oscillation.

The motion usually starts in a chaotic fashion at the distal ends of the spine, then it propagates caudally, until it settles in a standing wave pattern, which can then undergo "period halving bifurcations," transitioning away from chaos. At that stage, no further digital stimulus is required. This indicates that the rhythmic movement is innervated by a Central Pattern Generator (CPG). A further confirmation of this CPG hypothesis is that two quadriplegic subjects have been able to sustain the so-called spinal wave.

Figure 1A:
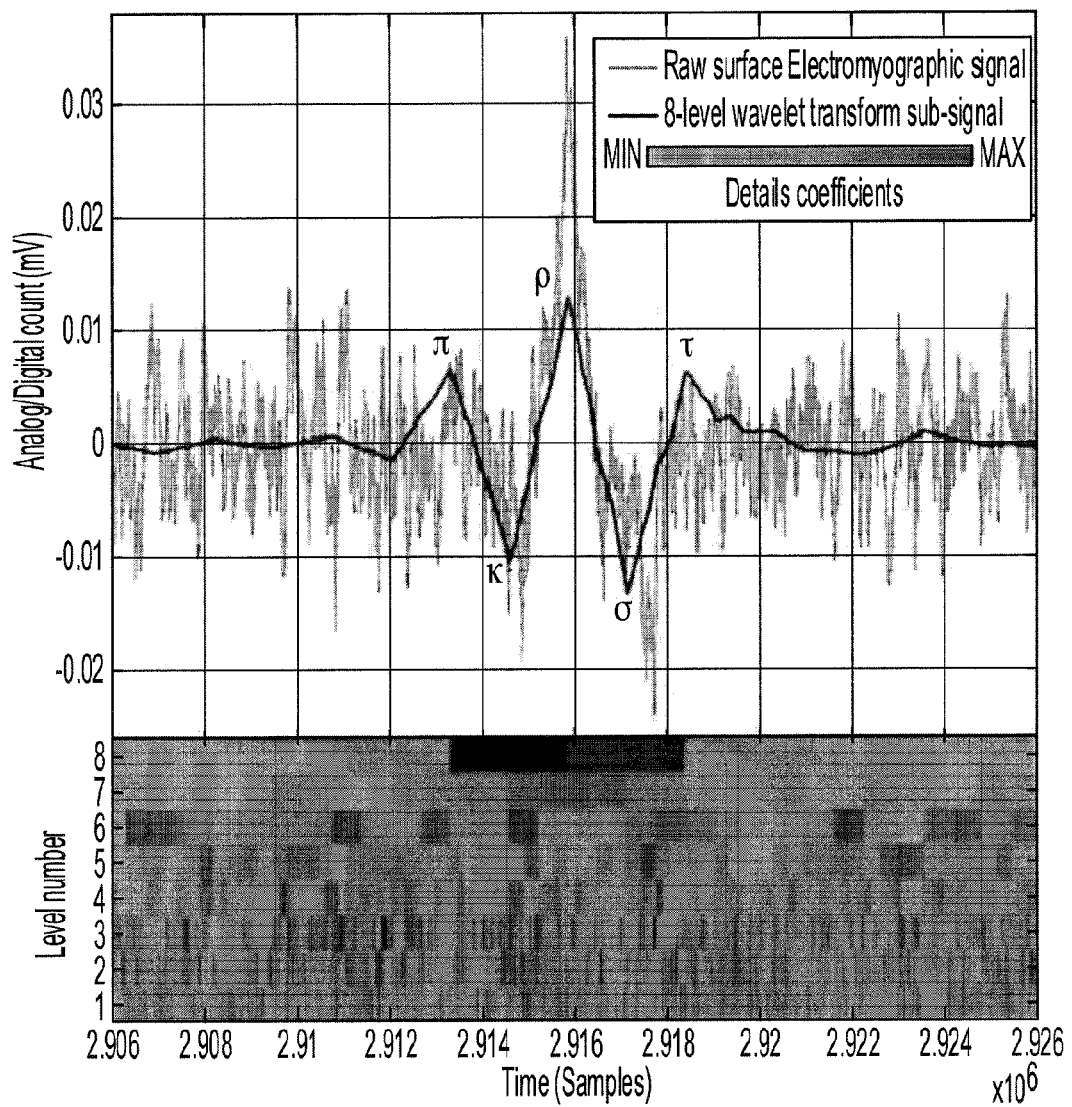
FIG. 1A illustrates a raw electromyographic signal overlaid with its wavelet transformed signal and its scalogram according to an aspect of the invention.

Besides CPG, another important aspect of this movement is coherence at a distance; the antinodes of the wave are indeed in coherent motion, with a wavelength in the order of approximately 1 meter (m), hence qualifying as coherence at a distance. The specificity of this CPG-innervated coherent motion may be confirmed by the Daubechies 3 (db3) wavelet decomposition of the sEMG signal. More specifically, the coherent motion may be confirmed by wavelet packets repeating themselves in an almost periodic fashion in the D8 subband of the wavelet decomposition, referred to as "D8 doublets" in view of being reconstructed from two adjacent relatively high detail coefficients at level 8, as shown in FIG. 1A. However, other wavelet decompositions may be used according to various embodiments.

FIG. 1A shows a raw paraspinal sEMG signal (first signal) of a healthy individual, overlaid with its 8-level wavelet transformed sub-signal (second signal) and its scalogram below. The D8 doublet is a precise sequence of (+) peaks and (−) valleys, defined as the $\pi$-$\kappa$-$\rho$-$\sigma$-$\tau$ sequence because of its similarity with the cardiac cycle (see FIG. 1B). The concordance between the D8 and a burst (specific burst) appears naturally without preprocessing. As shown, the two D8 coefficients indicate rapid succession of two Motor Unit Action Potentials (MUAPs).

For the reason that the surface electromyography is a superposition of MUAP trains, it remains unclear whether the observed D8 doublets are two discharges of the same motor units, or single discharges of different motor units firing successively in a rhythmic manner. In either case, the observed D8 doublet waveforms may represent a highly synchronized rhythmic spiking phenomenon of motor units that would conform to the definition of an "exceptional doublet" if two firings are coming from the same motor neuron, "exceptional" in the sense of large intradoublet interspike interval.

The interspike period of approximately 60 milliseconds (ms), as measured peak-to-peak from the D8 doublet waveform, exceeds the conventional limits of 2-20 ms according to the standardization of doublets set by the American Association of Neuromuscular & Electrodiagnostic Medicine. However, it has been reported that the standard range of doublets can be exceeded as Piotrkiewicz et al. reported exceptional doublets with 37 ms of intradoublet time in the human soleus muscle.

Furthermore, the Discrete Wavelet Transform (DWT) has also served to obtain the entire spiking event duration of approximately 130 ms measured from onset to offset of this wavelet waveform at scale 8, which spans the time comprised by two relatively high detailed coefficients at this scale.

Figure 1B:
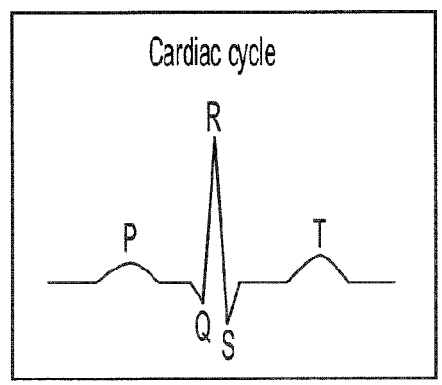
FIG. 1B illustrates a cardiac cycle according to an aspect of the invention.
Figure 2:
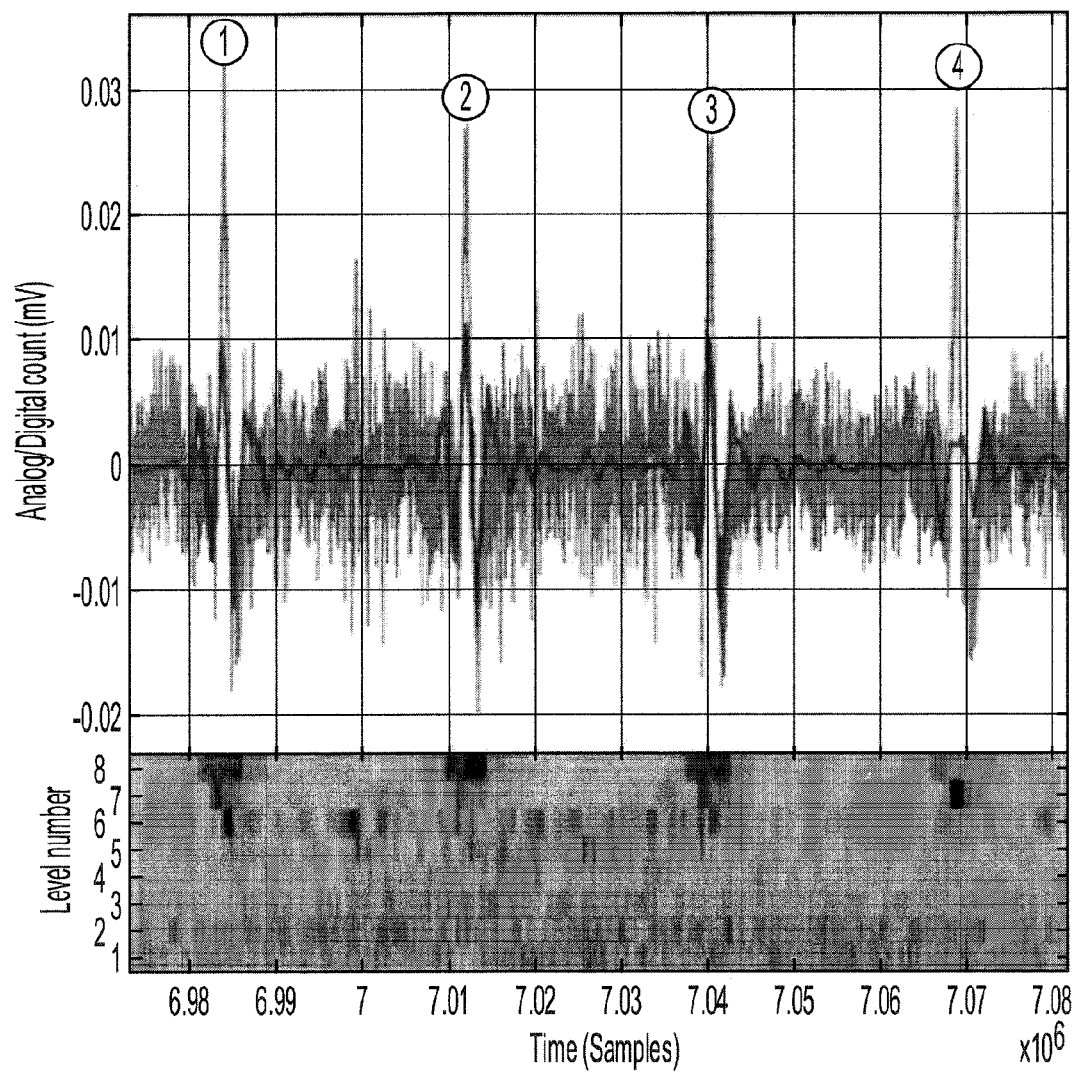
FIG. 2 illustrates a raw electromyographic signal overlaid with its wavelet transformed signal and its scalogram with no time delay according to an aspect of the invention.
Figure 3:
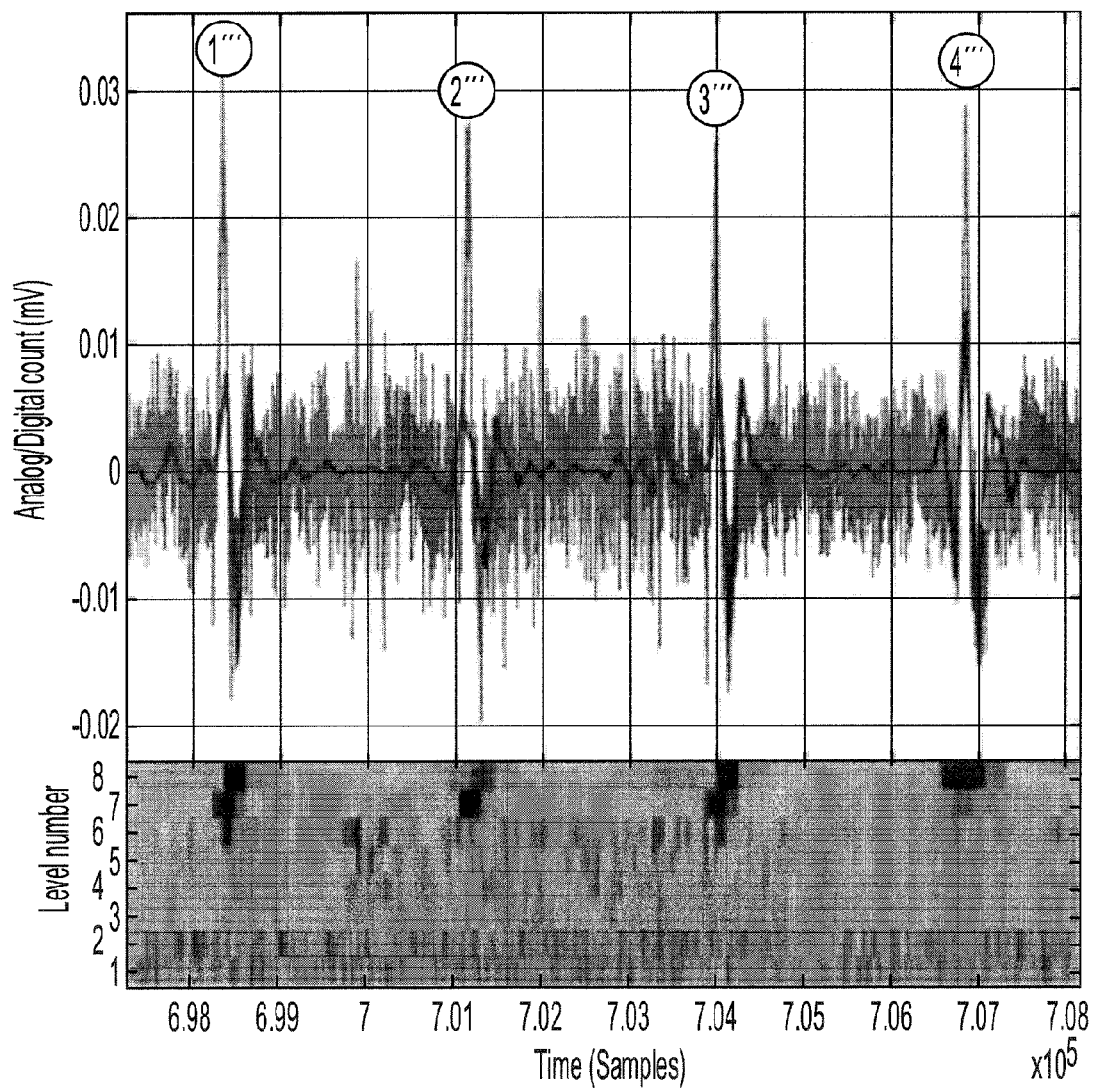
FIG. 3 illustrates a fourth specific burst within the graph of FIG. 2 with an applied 15 millisecond time delay according to an aspect of the invention.

Besides these early findings, the crucial observation is the near-synchrony between the onsets of the D8 doublets observed on the D8 traces and the onsets of the bursts of accrued sEMG activity visible on the raw signal traces, as shown in FIGS. 1A-1B and 2. FIG. 2 shows the raw thoracic sEMG signal of a subject, control subject 4, overlaid with its 8-level wavelet transformed sub-signal and its scalogram below. As shown, the first, second, and third bursts (specific bursts) are matching the specific bursts in the raw sEMG signal and the 8-level sub-signal more closely than the fourth burst (specific burst). FIG. 3 shows the graph of FIG.

2 with a 15 ms delay (time delay) applied to the fourth burst for closer matching between the raw sEMG signal and the 8-level sub-signal.

Figure 4A:
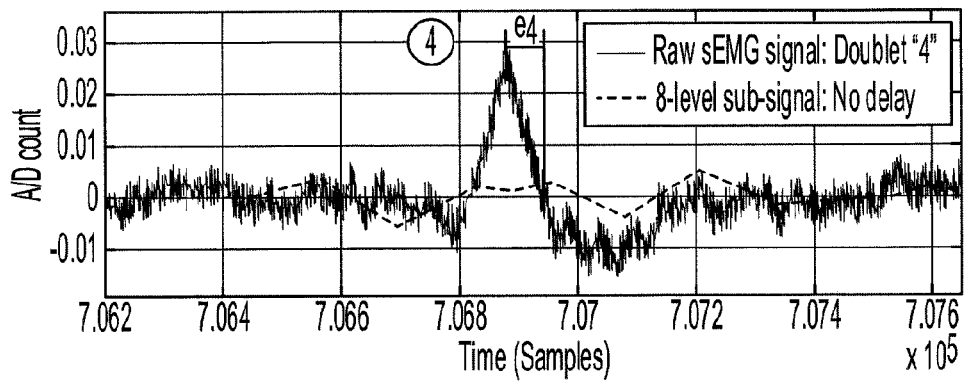
FIGS. 4A-4D illustrate the fourth specific burst within the graph of FIG. 2 with various time delays applied according to an aspect of the invention.
Figure 4B:
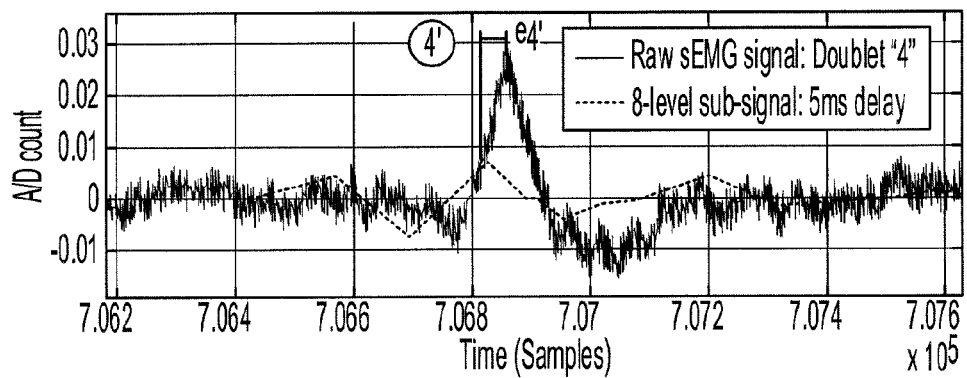
Figure 4C:
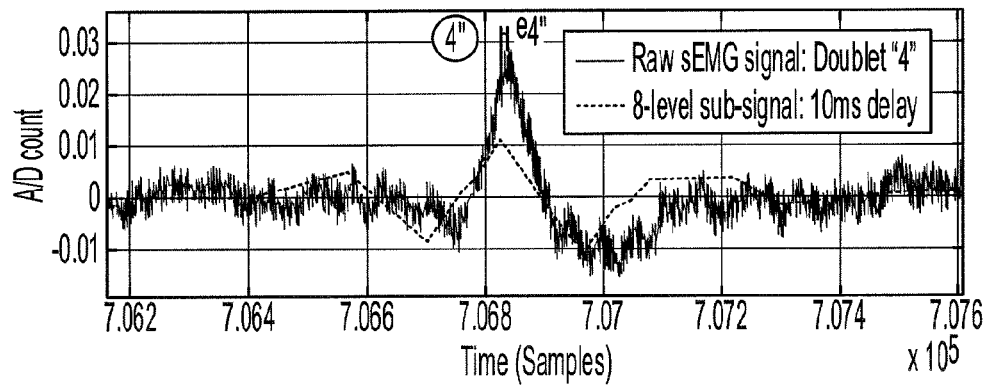
Figure 4D:
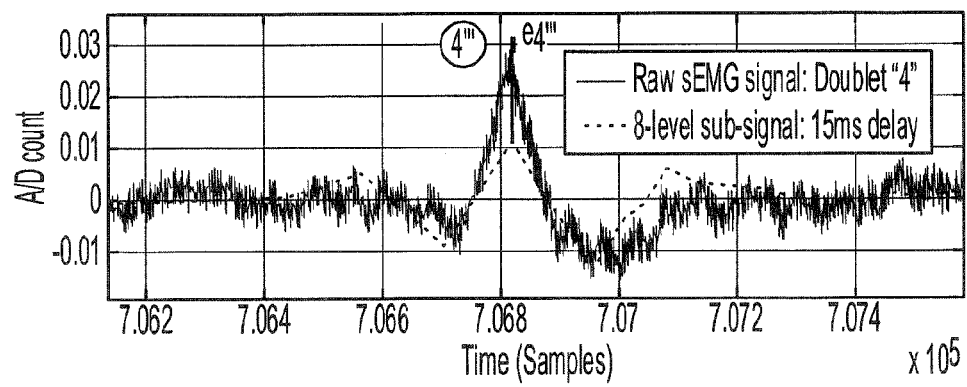

The recovery and matching between the fourth burst and its D8 doublet are further shown in FIGS. 4A-4D. FIGS. 4A-4D depict the raw thoracic surface electromyographic signal of the subject, control subject 4, centered around the fourth burst, D8 doublet 4, of FIGS. 2-3 superimposed with its 8-level wavelet transformed sub-signal. FIG. 4A. shows no delay to the raw sEMG signal before wavelet processing. FIG. 4B shows a 5 ms delay to the raw sEMG signal before wavelet processing. FIG. 4C shows a 10 ms delay to the raw sEMG signal before wavelet processing. FIG. 4D shows a 15 ms delay to the raw sEMG signal before wavelet processing. The peak time errors of ρ-wave are $|e_4|>|e_{4'}|>|e_{4''}|>|e_{4'''}|$. Peak time errors of the ρ-wave being the temporal distance between a peak (local maximum) between the raw sEMG signal and its corresponding peak (local maximum) in its 8-level wavelet transformed sub-signal.

This demonstrates that the D8 doublet with the smallest error (4'''), shown in FIG. 4D, belongs to the Pareto-optimal front, whereas D8 doublets 4, 4', and 4" do not. The Pareto optimality being the process of allocating the most efficient set of values that produces the lowest errors between the raw sEMG and its 8-level wavelet transformed sub-signal for each specific burst. A point representing a plurality of objectives to be optimized is on the Pareto-optimal front if any attempt to improve one of the objectives results in a deterioration of another objective.

The "nearness" of the time localizations of the D8 doublets and the bursts is crucial here. Indeed, by definition of the wavelet decomposition, the repetition of the DWT frame generating the D8 subband is periodic, while the sequence of bursts is not. Therefore, some time-shifting of the raw signal trace may be necessary to acquire a good waveform matching between a specific burst of the raw signal and its corresponding specific burst in the 8-level wavelet transformed sub-signal, D8 doublet. This time-shifting may be different from one specific burst to the other, leading to a variability of the time interval between successive bursts, which is referred to as Bursting Rate Variability (BRV).

The empirical distribution of the time intervals between successive bursts differ from one subject to another, but the types of continuous probability distributions already differentiates the BRV of quadriplegic subjects (see FIGS. 8A-8B) versus control subjects (see FIGS. 7A-7D). The quadriplegic subjects consistently presented the Weibull distribution as the best fit and mixtures of normal distributions in the case of control subjects. This discrepancy already points to some neurophysiological applications of BRV.

For the experimental results, a population of 9 volunteers, 7 control (healthy) and 2 quadriplegic subjects (presenting a total of around 8,000 D8 doublets) were chosen, the latter subjects with a cervical spinal cord injury at the C5 vertebral level. To draw an objective comparison between quadriplegic and control subjects, every quadriplegic subject had its recording taken during the same session as a control subject. Before recordings, the subjects had signed the Informed Consent drafted by the investigators and approved by the University Park Campus (UPC) Institutional Review Board (IRB) of the University of Southern California (USC).

The data utilized has been recorded over a period of a little more than 10 years. All along those recordings, a consistent recording protocol was followed: Surface electromyography (sEMG) reduced-noise tripolar electrodes ("Uni Patch Tyco EMG Electrodes Round Disk 7500 2.25 diameter Ag snaps" with two inputs to a differential amplifier and one grounding electrode) were placed at cervical (C2-C3), thoracic (T4-T6), lumbar (L3), and sacral (S2-S4) positions; all with the same sampling rate of 4,000 samples per second. The sensitive input prongs of the front-end electronics were initially at a 45-deg. angle with the muscle fibers and subsequently aligned with the back-muscle fibers, without significant difference observed in the results.

The most recent (<4 years) recordings were made with an Insight Discover sEMG station together with a Measurement Computing™ USB-1608FS device for analog-to-digital conversion, while the earlier recordings (10 years ago) were done with an Insight Millennium sEMG station interfaced with a Computer Board PCMCIA DAS16/16 card analog-to-digital converter.

The Daubechies 3 (db3) wavelet decomposition was used because it was discovered that its D8 subband provided the best correlations among the subband signals at different points along the spine (hence promoting the "coherence at a distance" aspect). Later, however, it was discovered that under some conditions the D7 subband was preferable. Because the mother function of the db3 mimics the MUAPs detected by the electrodes, the db3 is an ideal tool for picking up relevant waveforms in an otherwise messy sEMG signal corrupted by noise and motion artifacts.

Furthermore, it was found that the D8 of the db3 allowed for accurate localization of sEMG bursts most of the time. A wavelet similar to db3, the Daubechies 4 (db4), did not provide satisfactory results as it failed to pick up the onset of some bursts as accurately as the db3 did it. Additionally, the db3 mother function adhered more to the "pointy" shape of observed crests and troughs of electromyographic bursts than the smoother db4 mother function. Another wavelet tested face-to-face against db3, the Daubechies 2 (db2), did not show clear boundaries between the bursts start and end points, compared to the db3.

To solve the "shift variance" problem of the DWT of many signals causing some of the D8 doublets not to have well-defined peaks and valleys (see D8 doublet 4 in FIG. 3), or causing the πκρστ peaks and valleys to be horizontally offset with respect to the raw sEMG (see the ρ-peak of D8 doublets 1 and 3 in FIG. 3), the sampling times of the wavelet coefficients may be shifted by delaying the time at which the DWT begins. This may make the coefficients span different sections of the same raw sEMG signal.

A matching increment of the π-wave, πκ-slope, κ-wave, κρ-slope, ρ-wave, ρσ-slope, σ-wave, στ-slope, and τ-wave with the raw sEMG burst around D8 doublet 4 of FIG. 2 may be obtained by omitting the first 20, 40, and 60 samples (see FIGS. 4A-4D) before wavelet processing. This may result in recovering the precise peak-dip sequence of the πκρστ complex of D8 doublet 4''' in the raw burst signal, until achieving the benchmark waveform match of FIG. 1A. Due to the variability in the occurrence of the bursts, the process of delaying the raw sEMG signal before wavelet processing to achieve optimal waveform matching may be different from one raw bursting waveform (specific burst) to another one.

FIG. 3 shows how the best-suited time delay for D8 doublet 4''' may not be the best suited for D8 doublets 1''', 2''', 3''', as compared with D8 doublets 1, 2, 3 of FIG. 3 where no time delay has been applied.

To make the above procedure optimal, the errors of this πκρστ waveform versus the associated sEMG burst may be gathered in a multi-objective optimization function, of which the Pareto front is identified using one or more expert rules. If a given delay for the πκρστ waveform parameters is on the Pareto-optimal front, as in FIG. 4D, then this may provide a good match; whereas if some delays are not on the Pareto-optimal front, as those in FIGS. 4A-4C, then they may not provide a good match.

The one or more expert rules may automatically obtain the minimal error between the ρ-wave locations of each D8 doublet and its raw burst (vertical lines in FIGS. 4A-4D). The one or more expert rules may consist of a series of nested conditional statements (if-then-else rules depicted in FIGS. 5A-5C) inside a for loop with index values that identify the chronological position of each D8 doublet appearing in the time series.

Due to the raw sEMG signal being corrupted with high-frequency noise, and in order to increase the precision in finding the times at local maxima for each D8 doublet, a Savitzky-Golay filter may first be applied to the raw sEMG before being processed by the one or more expert rules. The Savitsky-Golay filter may increase the signal-to-noise ratio by fitting successive data points with a polynomial. However, other filters may be used interchangeably according to various embodiments. For example, at least one of a Kalman filter or a Laplacian smoothening may be used.

The number "d" of testing delays to exemplify the waveform matching technique may be preset to 3, where values of 5 ms, 10 ms, and 15 ms may be assigned for each delay time. However, other numbers of d testing delays may be used interchangeably according to various embodiments. The one or more expert rules may also consider the case of no delay time for the D8 doublets that are naturally matched with the sEMG bursts, which is represented with a zero-delay time. The whole sEMG signal processing technique, from data collection to probability distribution fitting, passing through multilayered 8-level DWT, smooth filtering, and the expert rules is depicted in the flowchart 500 of FIGS. 5A-5C.

Figures 1, 5A:
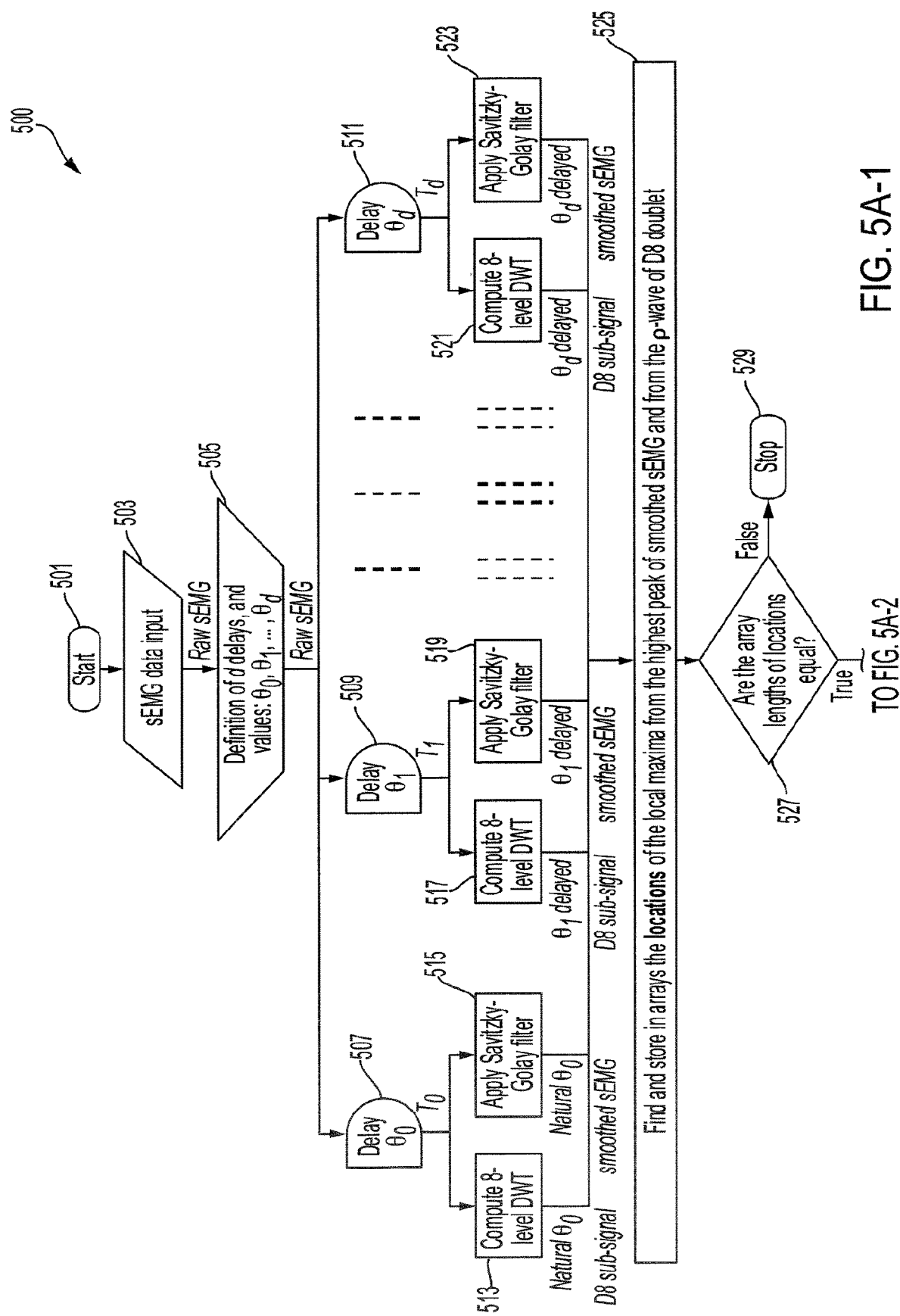
FIGS. 5A-5C illustrate flow diagrams of one or more expert rules according to an aspect of the invention.
Figures 2, 5A:
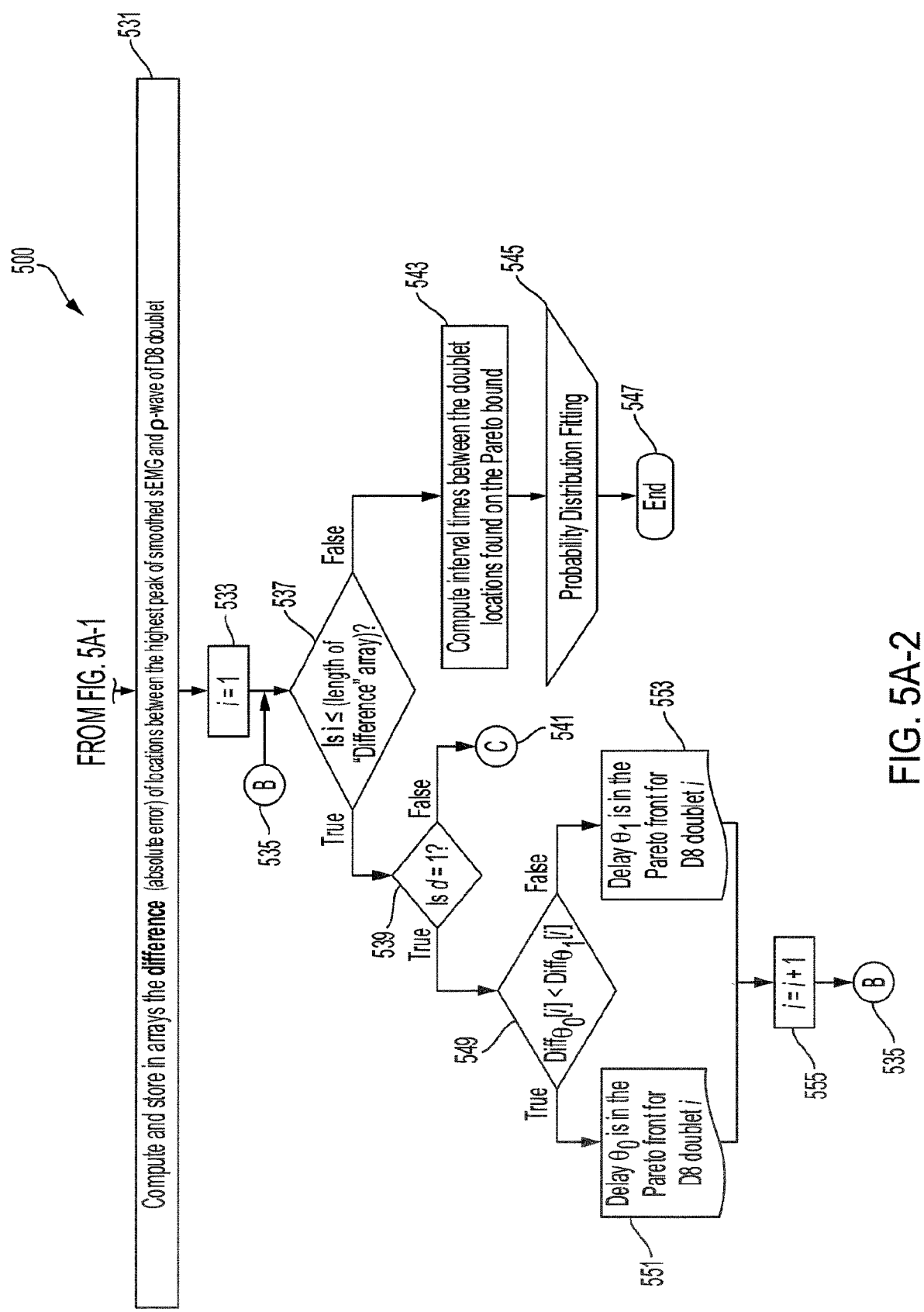
Figure 5B:
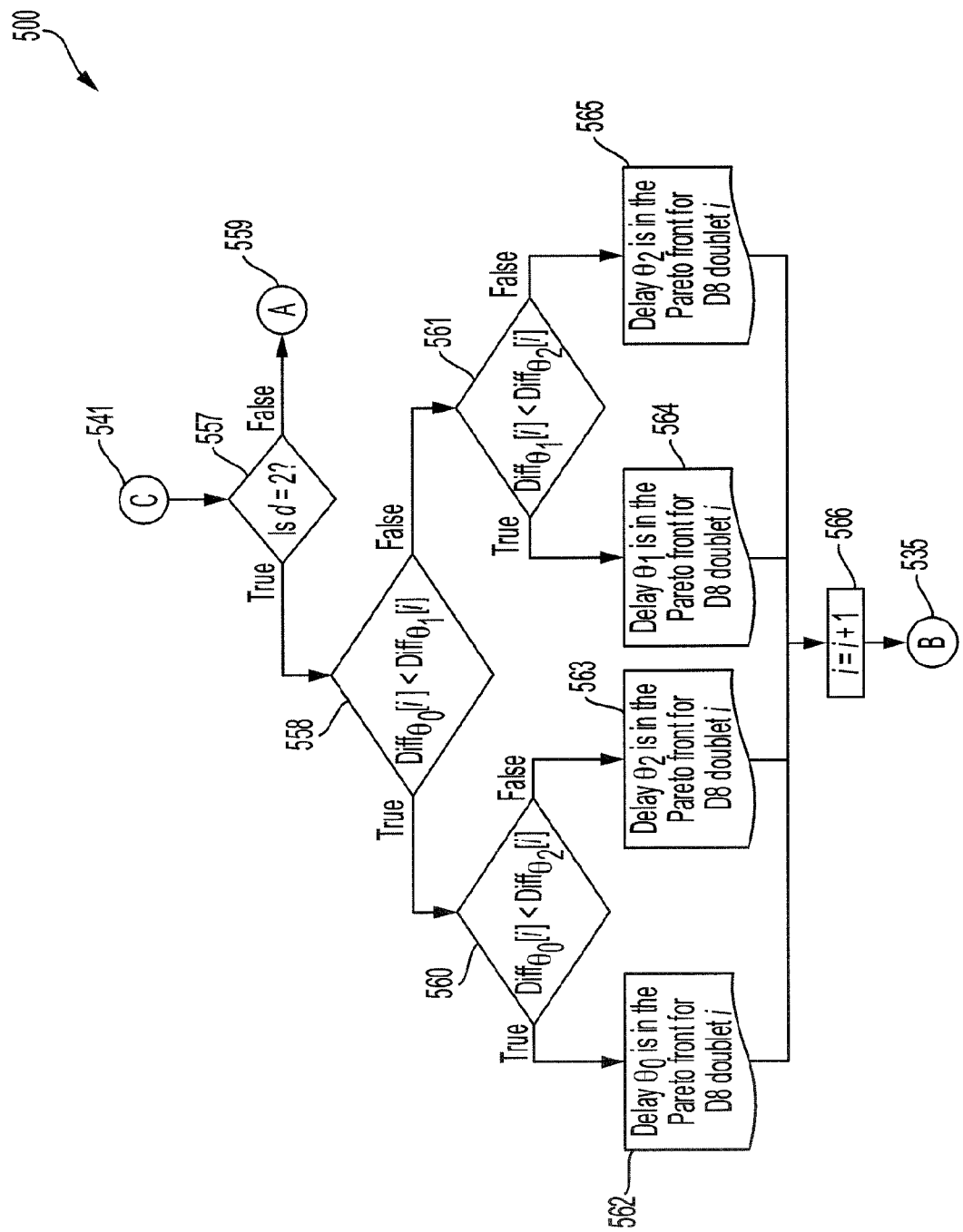
Figure 5C:
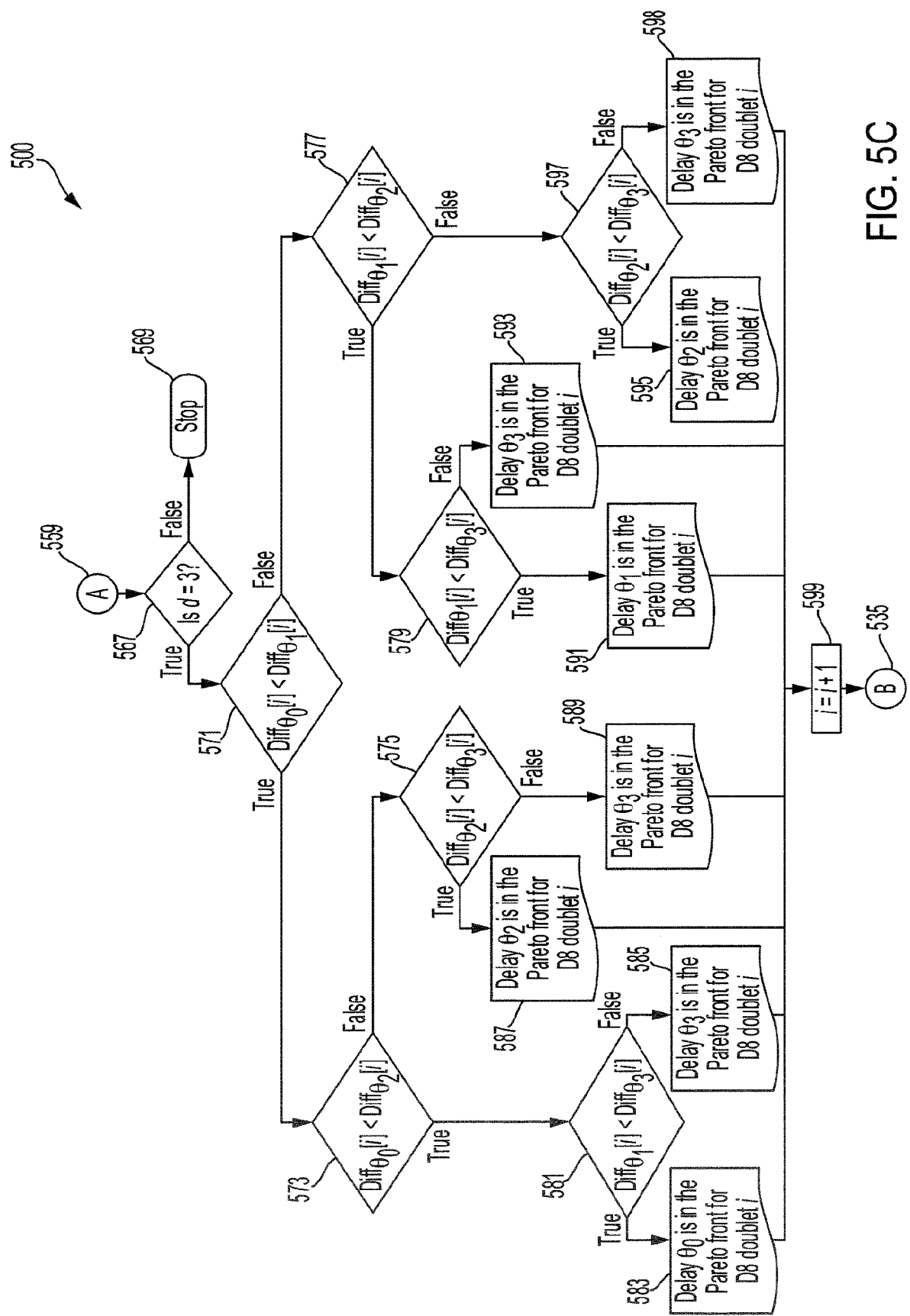

FIGS. 5A-5C depict a flowchart 500 for the one or more expert rules. The one or more expert rules may find the minimal error between local maxima of the sEMG burst and p-wave of its 8-level sub-signal (see FIGS. 4A-4D) among the (d+1) pairs of signal that come from the same sEMG trace. This may enhance the waveform matching and may provide the Pareto front ρρ-interval times (and/or ρ-wave magnitudes) for probability distribution analysis.

FIG. 5A shows the first flowchart of flowchart 500 for the one or more expert rules. According to various embodiments, the process depicted in flowchart 500 may be executed by a processor (e.g. processor 1609). The process may begin at step 501. A first signal in the form of an sEMG signal may be received by the processor (503). A definition of d delays and values for $\theta_0, \theta_1 \ldots \theta_d$ (one or more predetermined time delays) may be inputted into the processor by a user (505). The discrete number of the one or more predetermined time delays being represented by d.

The first predetermined time delay $\theta_0$ may be applied to the sEMG signal by the processor (507). The processor may then compute the 8-level DWT (second signal) from the sEMG signal with the predetermined time delay $\theta_0$ applied to it (513). A Savitsky-Golay filter may be applied to the sEMG signal with the applied predetermined time delay $\theta_0$ (515). The second predetermined time delay $\theta_1$ may be applied to the sEMG signal by the processor (509). The processor may then compute the 8-level DWT (second signal) from the sEMG signal with the predetermined time delay $\theta_1$ applied to it (517). A Savitsky-Golay filter may be applied to sEMG signal with the applied predetermined time delay $\theta_1$ (519). The last predetermined time delay $\theta_d$ may be applied to the sEMG signal by the processor (511). The processor may then compute the 8-level DWT (second signal) from the sEMG signal with the predetermined time delay $\theta_d$ applied to it (521). A Savitsky-Golay filter may be applied to sEMG signal with the applied predetermined time delay $\theta_d$ (523).

After computing the above, the processor may find and store in arrays the locations of the local maxima from the highest peak of smoothed sEMG and from the ρ-wave of the D8 doublet (525). The processor may then device if the array lengths of the locations are equal at decision branch (527). If they are not, the process flow stops (529). If they are, the process flow may continue with the processor computing and storing in arrays the difference (absolute error) of locations between the highest peak of smoothed sEMG and ρ-wave of D8 doublet (531).

The process continues with the first D8 doublet i (i=1) (e.g. the first burst) (533). The processor may decide if i≤the length of "difference" array (537). Additionally, the results of process node B may continue here as well (535). If i is not less than or equal to the length of "difference" array, the processor may compute interval times between the doublet locations found on the Pereto bound (543). The processor may then compute a probability distribution fitting (545) and then the process ends (547). If i is less than or equal to the length of "difference" array, the processor may determine if d is the first predetermined delay "d=1" (539). If d is not the first predetermined delay, the processor may then continue to process Node C (541). If d is the first predetermined delay, the processor may then determine if the length of the "Difference" (temporal distance) for time delay $\theta_0$ is less than the length of "Difference" for time delay $\theta_1$ (549). If the length of the "Difference" for time delay $\theta_0$ is less than the length of "Difference" for delay time $\theta_1$, then the processor may determine that that time delay $\theta_0$ is in the Pareto front for D8 doublet i (551). If the length of the "Difference" for time delay $\theta_0$ is not less than the length of "Difference" for time delay $\theta_1$, then the processor may determine that that time delay $\theta_1$ is in the Pareto front for D8 doublet i (553). The process may then move onto the next sequential D8 doublet (555) and then onto process Node B (535).

FIG. 5B is a continuation of the flowchart 500. The process may continue with process Node C 541. The processor may determine if d is the second predetermined time delay "d=2" (557). If d is not the second predetermined time delay, the processor may move onto process Node A (559). If d is the second predetermined time delay, the processor may then determine if the length of the "Difference" for time delay $\theta_0$ is less than the length of the "Difference" for time delay $\theta_1$ (558). If the length of the "Difference" for time delay $\theta_0$ is less than the length of the "Difference" for time delay $\theta_1$, then the processor may determine if the length of the "Difference" for time delay $\theta_0$ is less than the length of the "Difference" for time delay $\theta_2$ (560). If the process determines that the length of the "Difference" for time delay $\theta_0$ is less than the length of the "Difference" for time delay $\theta_2$, then the process determines that time delay $\theta_0$ is in the Pareto front for D8 doublet i (562). If the processor determines that the length of the "Difference" for time delay $\theta_0$ is not less than the length of the "Difference" for time delay $\theta_2$, then the processor may then determine that time delay $\theta_2$ is in the Pareto front for D8 doublet i (563).

If the length of the "Difference" for time delay $\theta_0$ is not less than the length of the "Difference" for time delay $\theta_1$, then the processor may determine if the length of the "Difference" for time delay $\theta_1$ is less than the length of the "Difference" for time delay $\theta_2$ (561). If the length of the "Difference" for time delay $\theta_1$ is less than the length of the "Difference" for time delay $\theta_2$, then the processor may determine that time delay $\theta_1$ is in the Pareto font for D8 doublet i (564). If the length of the "Difference" for time delay $\theta_1$ is not less than the length of the "Difference" for time delay $\theta_2$, then the processor may determine that time delay $\theta_2$ is in the Pareto font for D8 doublet i (565). After the results of steps 562, 563, 564, and 565, the processor may then move onto the next sequential D8 doublet (566) and then onto process Node B (535).

FIG. 5C is a continuation of the flowchart 500. The process continues with process Node A (559). The processor may determine if d is the third predetermined time delay "d=3" (567). If d is not the third predetermined time delay, the process stops (569). If d is the third predetermined time delay, the processor may then determine if the length of the "Difference" for time delay $\theta_0$ is less than the length of the "Difference" for time delay $\theta_1$ (571). If the length of the "Difference" for time delay $\theta_0$ is less than the length of the "Difference" for time delay $\theta_1$, then the processor may determine if the length of the "Difference" for delay time $\theta_0$ is less than the length of the "Difference" for time delay $\theta_2$ (573). If the processor determines that the length of the "Difference" for time delay $\theta_0$ is less than the length of the "Difference" for time delay $\theta_2$, then the processor may determine if the length of the "Difference" for time delay $\theta_0$ is less than the length of the "Difference" for time delay $\theta_3$ (581). If the processor determines that the length of the "Difference" for time delay $\theta_0$ is less than the length of the "Difference" for time delay $\theta_3$, then the processor may determine that time delay $\theta_0$ is in the Pareto front for D8 doublet i (583). If the processor determines that the length of the "Difference" for time delay $\theta_0$ is not less than the length of the "Difference" for time delay $\theta_3$, then the processor may determine that time delay $\theta_3$ is in the Pareto front for D8 doublet i (585).

If the processor determines that the length of the "Difference" for time delay $\theta_0$ is not less than the length of the "Difference" for time delay $\theta_2$, then the processor may determine if the length of the "Difference" for time delay $\theta_2$ is less than the length of the "Difference" for time delay $\theta_3$ (575). If the processor determines that the length of the "Difference" for time delay $\theta_2$ is less than the length of the "Difference" for time delay $\theta_3$, then the processor may determine that time delay $\theta_2$ is in the Pareto front for D8 doublet i (587). If the processor determines that the length of the "Difference" for time delay $\theta_2$ is not less than the length of the "Difference" for time delay $\theta_3$, then the processor may determine that time delay $\theta_3$ is in the Pareto front for D8 doublet i (589).

If the length of the "Difference" for time delay $\theta_0$ is not less than the length of the "Difference" for time delay $\theta_1$, then the processor may determine if the length of the "Difference" for time delay $\theta_1$ is less than the length of the "Difference" for time delay $\theta_2$ (577). If the processor determines that the length of the "Difference" for time delay $\theta_1$ is less than the length of the "Difference" for time delay $\theta_2$, then the processor may determine if the length of the "Difference" for time delay $\theta_1$ is less than the length of the "Difference" for time delay $\theta_3$ (579). If the processor determines that the length of the "Difference" for time delay $\theta_1$ is less than the length of the "Difference" for time delay $\theta_3$, then the processor may determine that time delay $\theta_1$ is in the Pareto front for D8 doublet i (591). If the processor determines that the length of the "Difference" for time delay $\theta_1$ is not less than the length of the "Difference" for time delay $\theta_3$, then the processor may determine that time delay $\theta_3$ is in the Pareto front for D8 doublet i (593).

If the processor determines that the length of the "Difference" for time delay $\theta_1$ is not less than the length of the "Difference" for time delay $\theta_2$, then the processor may determine if the length of the "Difference" for time delay $\theta_2$ is less than the length of the "Difference" for time delay $\theta_3$ (597). If the processor determines that the length of the "Difference" for time delay $\theta_2$ is less than the length of the "Difference" for time delay $\theta_3$, then the processor may determine that time delay $\theta_2$ is in the Pareto front for D8 doublet i (595). If the processor determines that the length of the "Difference" for time delay $\theta_2$ is not less than the length of the "Difference" for time delay $\theta_3$, then the processor may determine that time delay $\theta_3$ is in the Pareto front for D8 doublet i (598). After the results of steps 583, 585, 587, 589, 591, 593, 595, and 598, the processor then moves onto the next sequential D8 doublet (599) and then onto process Node B (535).

There may be two ways to construct the histogram of the time between the ρ-waves of successive D8 doublet waveforms, or "return time" for short. First, in one procedure there may be included in the sample set only those ρρ-intervals between ρ-waves that are naturally matched with their corresponding bursts (without time shifting), discarding those that do not appear to match, such as D8 doublet 4 of FIG. 2. However, some D8 doublets might appear to naturally match with their sEMG bursts, for instance, D8 doublets 1 and 3 of FIG. 2, and considering the ρ-wave locations of these two D8 doublets would add undesired observational systematic errors to the distribution fit analysis since a better match was found by the one or more expert rules (see D8 doublets 1' and 3' of FIGS. 7A-7D). These unwanted errors can be eliminated in the other "enhanced" procedure achieved with the one or more expert rules and the time-shifted DWT at various time delays. The latter procedure may be preferred according to various embodiments. In the enhanced procedure, the histogram may be constructed with accrued accuracy with ρρ-intervals after optimal (on the Pareto-optimal front) time shifting to match all bursts with their respective D8 doublets. The latter, by the same token, may also increase the sample size.

Figures 6A, 6B, 6C, 6D:
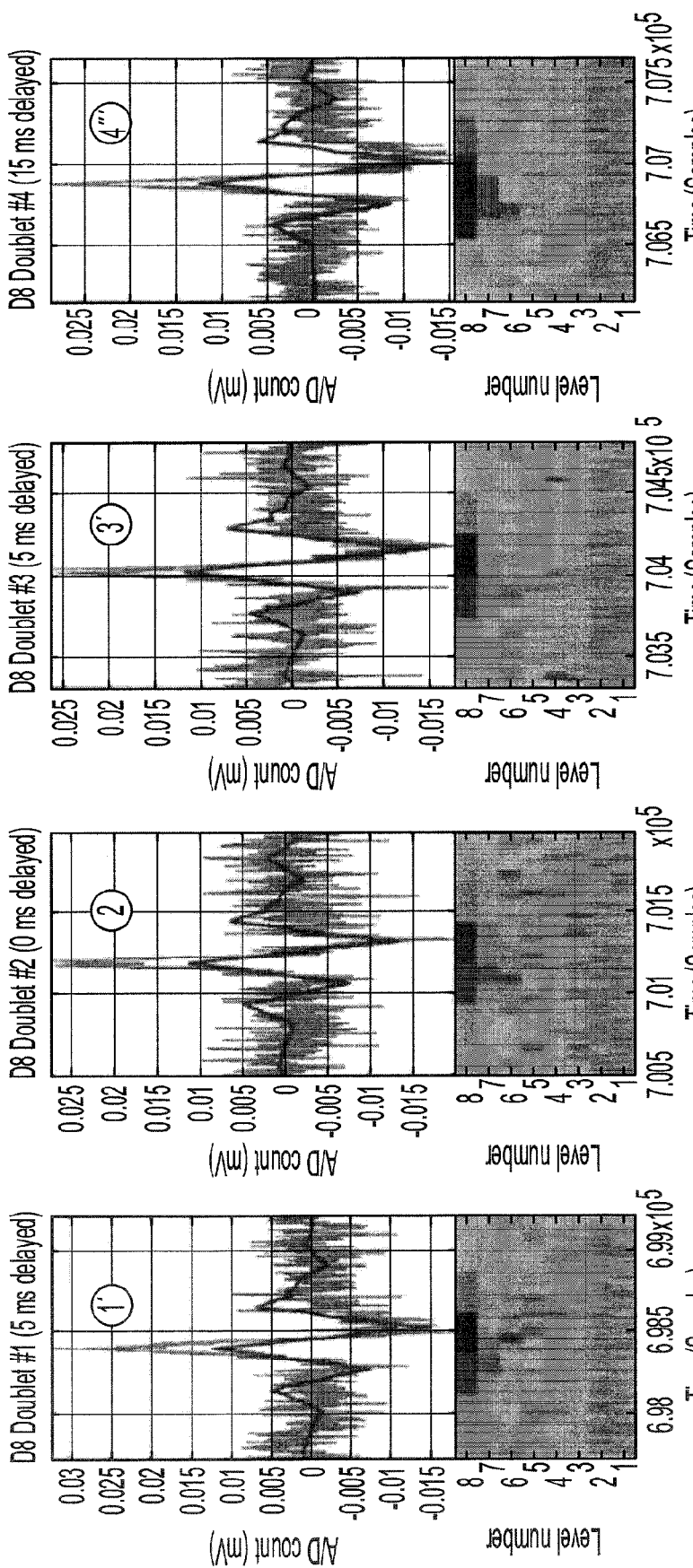
FIGS. 6A-6D illustrate each specific burst within the graph of FIG. 2 and FIG. 3 with various time delays applied according to an aspect of the invention.

FIGS. 6A-6D show individual specific bursts of a raw thoracic sEMG trace of subject 4 overlaid with its 8-level sub-signal and its scalogram below. FIG. 6A shows D8 Doublet 1 with a Pareto front time delay of 5 ms. FIG. 6B shows D8 Doublet 2 with a Pareto front time delay of 0 ms. FIG. 6C shows D8 Doublet 3 with a Pareto front time delay of 5 ms. FIG. 6D shows D8 Doublet 4 with a Pareto front time delay of 15 ms. As depicted, there may be instances where the sEMG trace may match with its 8-level sub-signal without a delay (see FIG. 6B). However, in other instances, an applied delay may provide a better match between the sEMG trace and its 8-level sub-signal (see FIGS. 6A, 6C, and 6D).

The statistical software SAS® Studio 3.4 and JMP Pro 13 (both by the SAS Institute) may be used to find the best theoretical probability distribution fit from the frequency histograms of D8 doublet return times based on the corrected Akaike Information Criterion (AICc) for model selection; the results are summarized in FIGS. 9A-9C, 10A-10C, and 11A-11C. In the case where the Weibull distribution was the best ranked in the AICc sense, it may also be checked for a goodness of fit using the Cramer-von Mises-W test. As for the best-ranked normal mixture distribution, the Pearson's chi-squared test may be used. In both cases, the null hypothesis ($H_0$) may state that the observed frequency distribution is consistent with the estimated theoretical distribution, and small p-values (<0.05) would reject $H_0$ in favor of the alternative hypothesis ($H_1$) that the data is not from the theoretical distribution.

Akaike's approach to finding the best probability distribution fit is a Maximum Likelihood Estimation technique that seeks to provide a measure of fitting relative to distinct probability models by estimating parameters that maximize their Likelihood function. The AICc, (correction for overfitting) may be defined as $$AICc = AIC + \frac{2k(k+1)}{n-k-1},$$

where n is the sample size, k is the number of parameters, and AIC=2k−2LogLikelihood($\theta$), where $\theta$ represents the parameters to be estimated for a given model. Let $X_1$, $X_2, \ldots, X_n$ be a set of continuous random samples with joint density function $f_\theta(x)$ depending on the parameters $\theta$. The Likelihood function $L(\theta)=f_\theta(x_1, x_2, \ldots, x_n)$, that may be written as $L(\theta|x)$, is the joint probability distribution $f_\theta(x_1, x_2, \ldots, x_n)$ with parameters $\theta$ of the set of n random variables evaluated at the observed values from the sample. Under the standard assumption of independent and identically distributed (i.i.d.) samples, the Likelihood function factors may be represented as $f_\theta(x_1)f_\theta(x_2) \ldots f(x_n)$. The LogLikelihood may represent the natural log of the Likelihood function, which may be preferred as it simplifies the calculations of critical values.

Since there is no prior knowledge of the underlying distribution of D8 doublet return times, the AICc, by means of estimating the parameters that provide the largest plausibility for obtaining the observed values for several probability models, may provide a point of comparison among the probability models that the samples are most likely to come from, serving as a means for model selection. Some of the models tested faceto-face in this sense include the Gamma, Weibull, Exponential, LogNormal, GLog, Johnson Su, Johnson Sl, Gaussian, and Normal 2 & 3 Mixture probability densities.

Akaike may reformulate the maximization of the Log-Likelihood function by working with its negative value (minimization of the LogLikelihood function), in such case, lower values of AICc denote better model fits. Since the AICc only provides a ranking among different types of distributions and does not warn for poorly fitted models, a Goodness-of-fit test for the model with the lowest AICc may complement this part of the model selection technique, ensuring that the best-ranked model represents a good fit. The two-parameter Weibull distribution ($\alpha$, $\beta$), is shown below as Equation 1.

$$f(x; \alpha, \beta) = \frac{\beta}{\alpha}\left(\frac{x}{\alpha}\right)^{\beta-1} e^{-\left(\frac{x}{\alpha}\right)^\beta}; \text{ for } \alpha, \beta > 0; x \geq 0, \quad \text{Equation 1}$$

In the above equation, $\alpha$ an $\beta$ are the scale and shape parameters, respectively. The above Weibull distribution was found to be the most robust at small sample sizes as it required the smallest sample size (n) to be identified as the best fit most of the trials (see FIGS. 12A-12D). For instance, at least n≈6 samples were required to achieve ~50% success rate for several values of $\alpha$ an $\beta$, compared with Gamma ($\lambda$=4; scale=1) with at least n≈26 with ~32% success rate, Gaussian ($\mu$=100; $\sigma^2$=302) with at least n≈130 with ~40% success rate, among others shown in FIGS. 13A-13D.

Figure 12B:
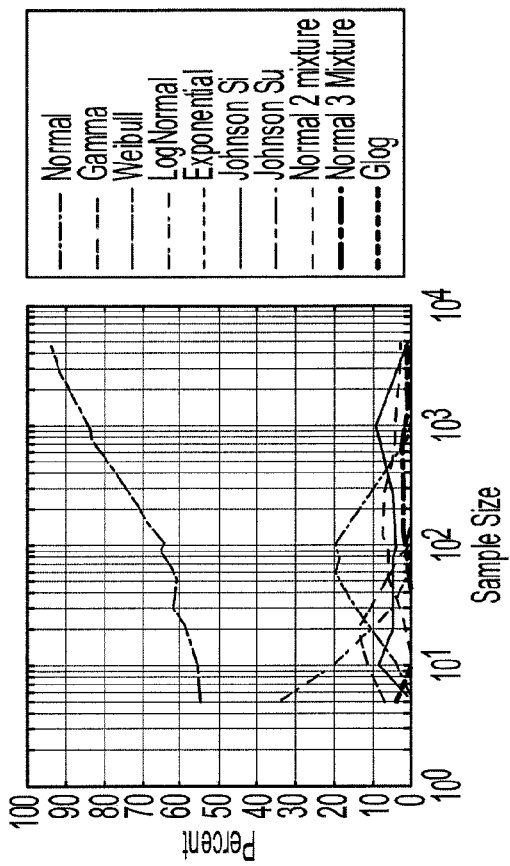
FIGS. 12A-12D illustrate a simulation of best fitting distributions at different sample sizes according to an aspect of the invention.
Figure 12D:
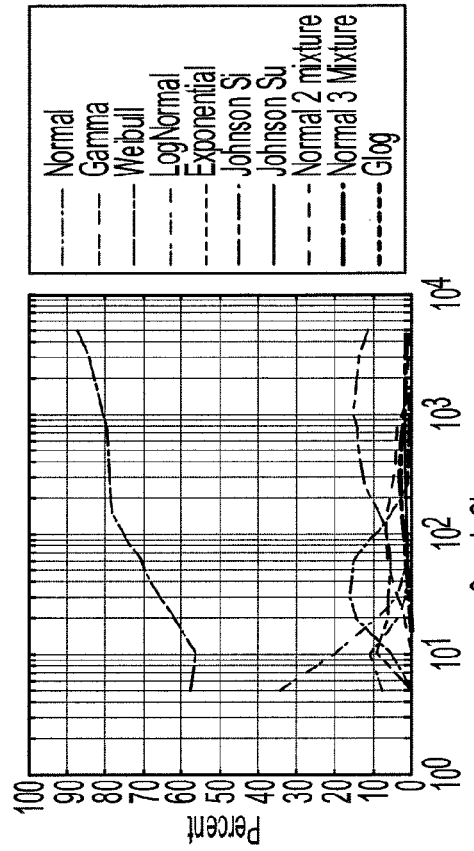
Figure 12A:
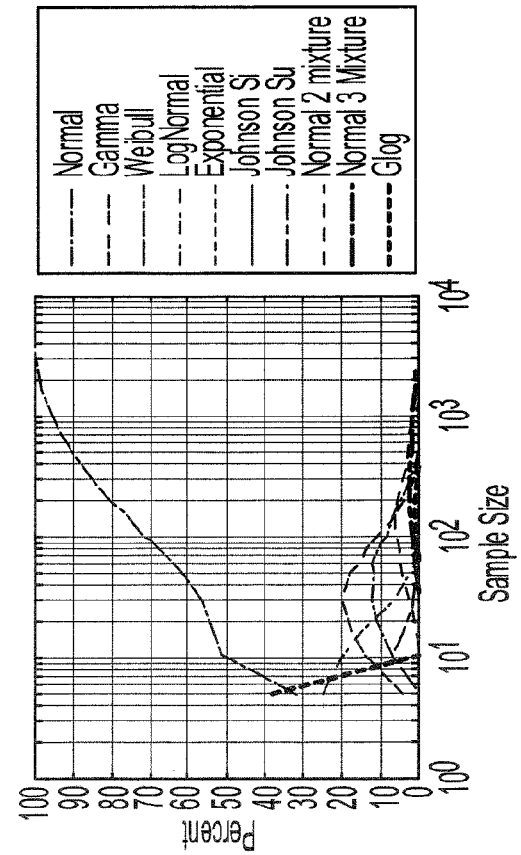

FIGS. 12A-12D show simulation of best fitting distributions at different sample sizes obtained with the smallest AICc value by randomly sampling from various sources. FIG. 12A show the best fitting distributions at different sample sizes obtained with the smallest AICc value by randomly sampling from a Weibull ($\beta$=2.86, $\alpha$=1.07) distribution. FIG. 12B show the best fitting distributions at different sample sizes obtained with the smallest AICc value by randomly sampling from a Weibull ($\beta$=5.13, $\alpha$=0.81) distribution.

Figure 12C:
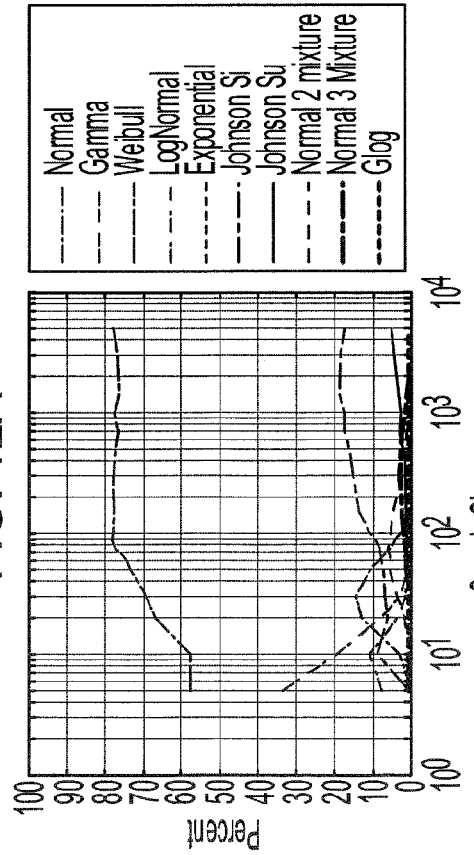

FIG. 12C show the best fitting distributions at different sample sizes obtained with the smallest AICc value by randomly sampling from a Weibull ($\beta$=26.14, $\alpha$=0.72) distribution. FIG. 12D show the best fitting distributions at different sample sizes obtained with the smallest AICc value by randomly sampling from a Weibull ($\beta$=9.04, $\alpha$=1.04) distribution. The Weibull distribution was identified as the best fit with at least ~5 samples with different parameters.

Due to the high robustness of the Weibull distribution at small sample sizes that was observed with simulations, it is not surprising that the Weibull distribution is widely applied in reliability tests, which is often hampered with small sample sizes.

Figure 13A:
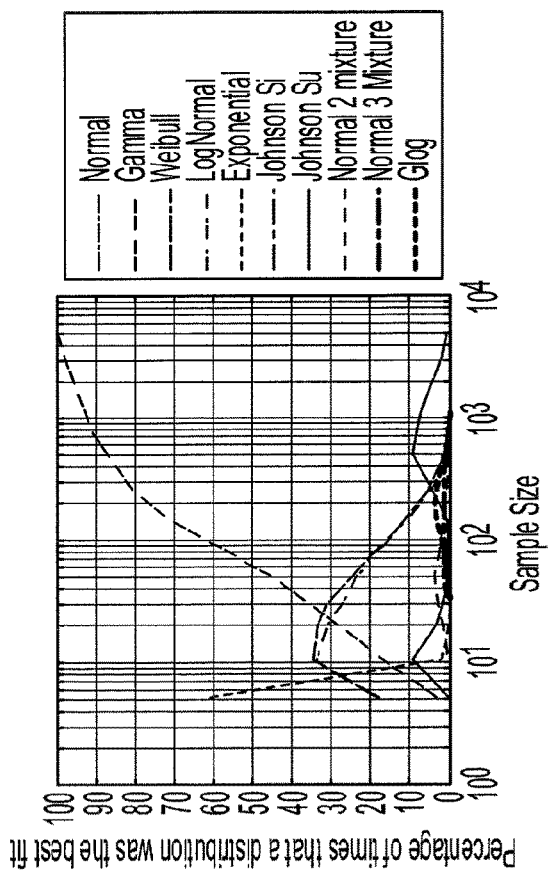
FIGS. 13A-13D illustrate a simulation of best fitting distributions at different sample sizes according to an aspect of the invention.
Figure 13B:
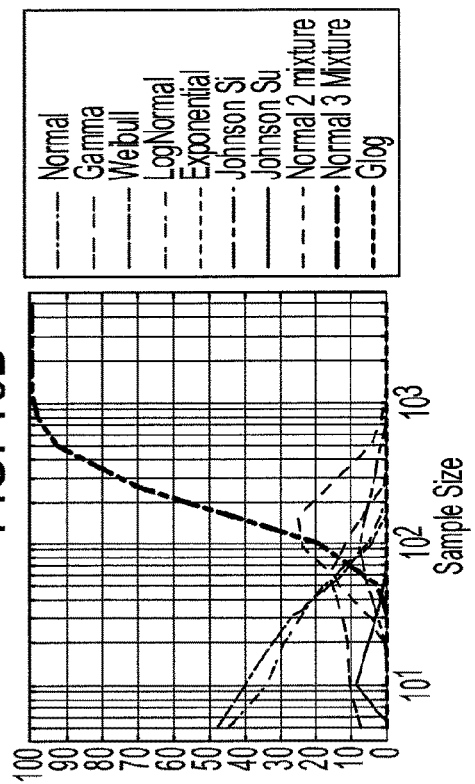

FIGS. 13A-13D show simulation of best fitting distributions at different sample sizes obtained with the smallest AICc values by sampling random numbers from various sources. FIG. 13A shows simulation of best fitting distributions at different sample sizes obtain with the smallest AICc values by sampling random numbers from the Normal ($\mu$=100, $\rho^2$=30$^2$) distribution. FIG. 13B shows simulation of best fitting distributions at different sample sizes obtain with the smallest AICc values by sampling random numbers from the Normal ($\lambda$=4, scale=1) distribution.

Figure 13C:
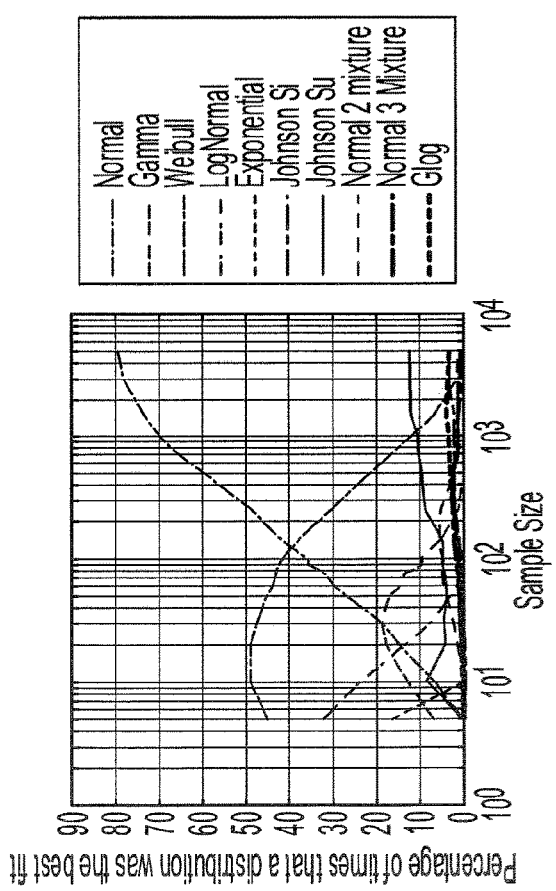
Figure 13D:
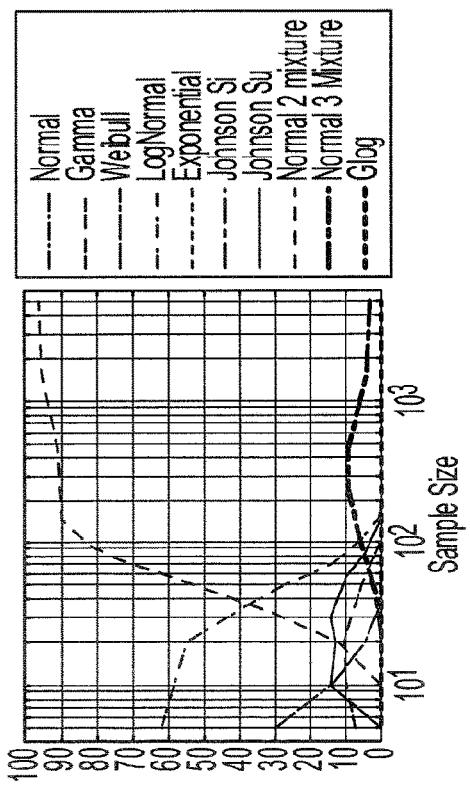

FIG. 13C shows simulation of best fitting distributions at different sample sizes obtain with the smallest AICc values by sampling random numbers from a Normal 2 Mixture distribution with parameters from those obtained in lumbar spine signal of subject 8. FIG. 13D shows simulation of best fitting distributions at different sample sizes obtain with the smallest AICc values by sampling random numbers from a Normal 3 Mixture distribution with parameters from those obtained in lumbar spine signal of subject 3. The correct (non-Weibull) distribution takes larger sample sizes (10$^2$) to be identified than it takes for the Weibull of FIGS. 12A-12D to be identified with just ~5.

Figure 14A:
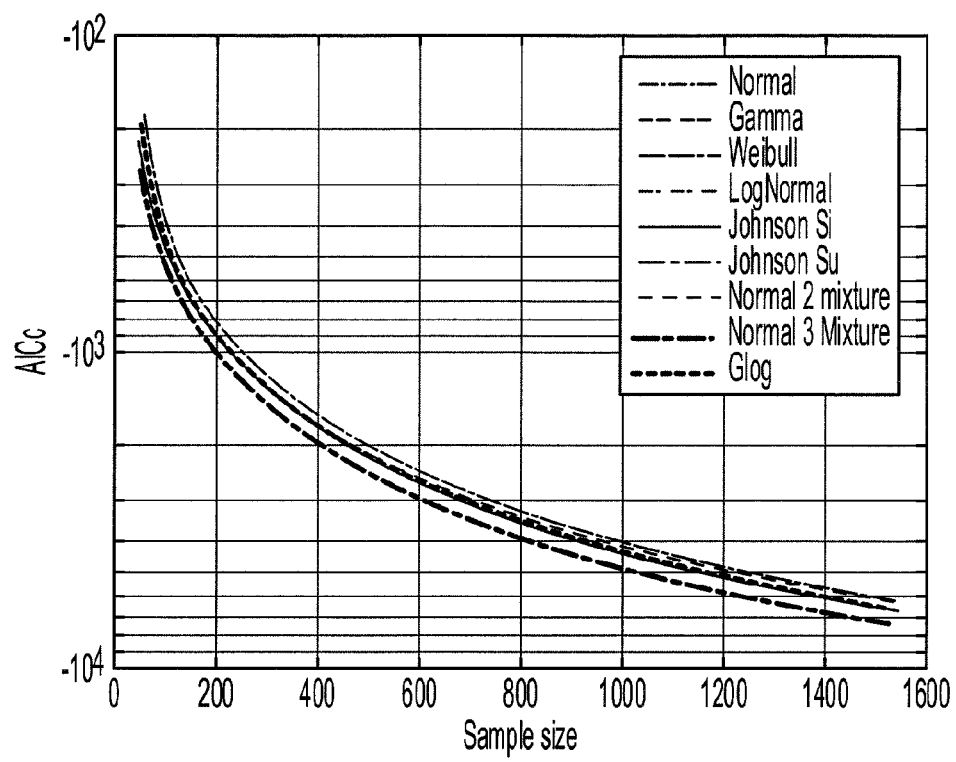
FIG. 14A illustrates corrected Akaike Information Criterion values versus sample size according to an aspect of the invention.
Figure 14B:
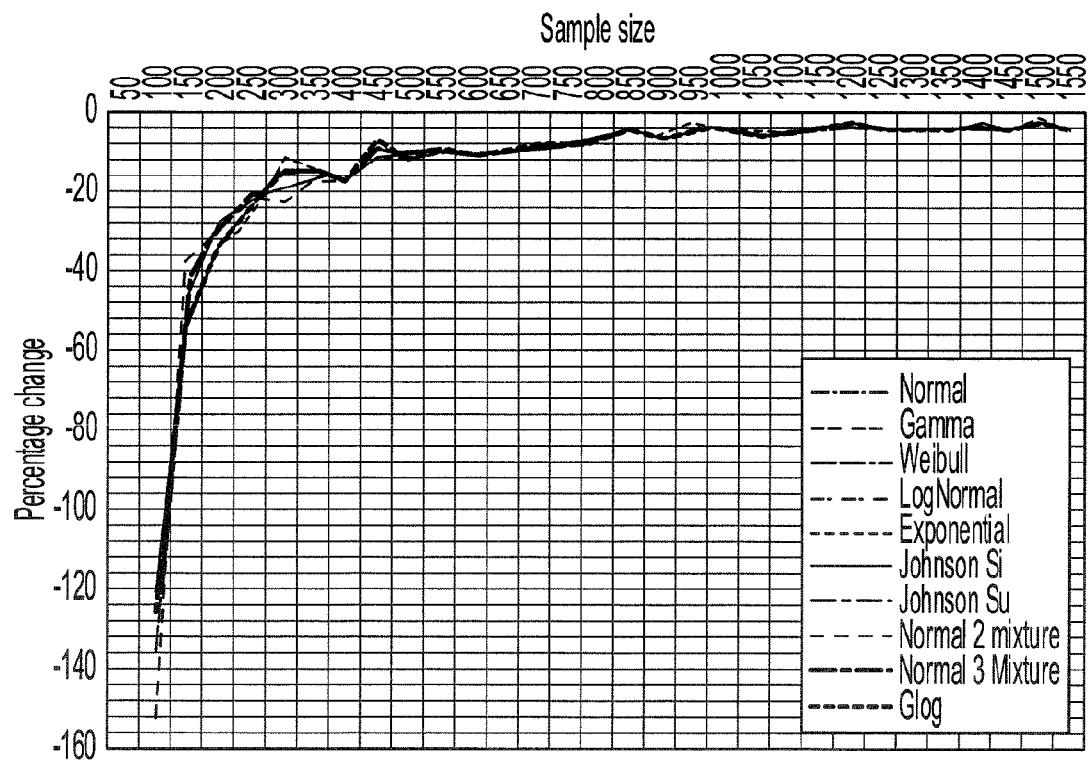
FIG. 14B illustrates percentage change of corrected Akaike Information Criterion values versus sample size according to an aspect of the invention.
Figure 15:
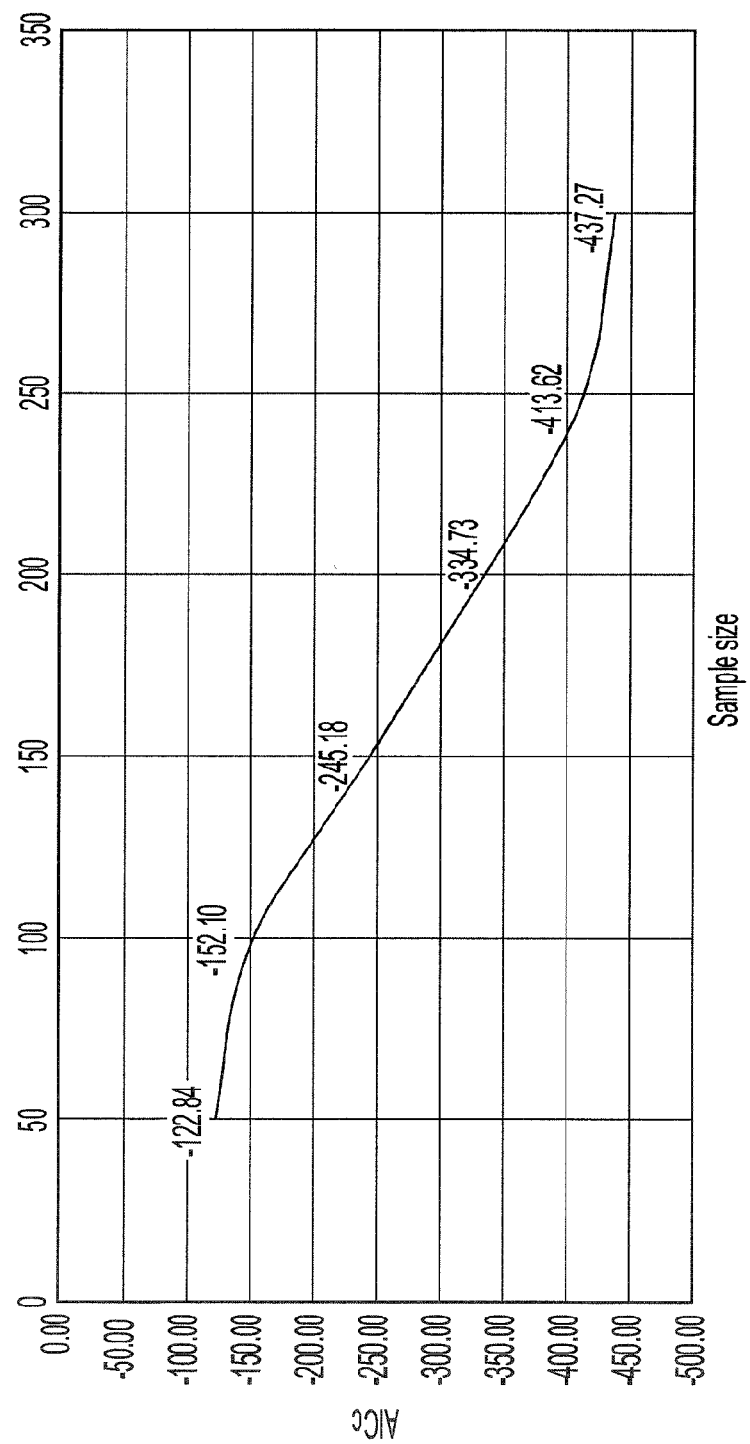
FIG. 15 illustrates corrected Akaike Information Criterion values versus sample size according to an aspect of the invention.

As regard to the maximum number of return times to consider in the distribution fitting analysis, a stopping rule can be determined when the AICc approaches a minimum value, meaning that the percentage change of AICc approaches zero as the sample size increases (see FIGS. 14A-14B and 15).

FIG. 14A shows the AICc values versus sample size (n) to determine a stopping rule for sample size. The sample size, depicted in FIG. 14A, is from the thoracic signal of subject 4. FIG. 14B shows the percentage change of AICc values at different sample sizes for thoracic signal of subject 4. FIG. 15 illustrates the AICc values versus sample size (n) to determine a stopping rule for sample size. The sample size depicted in FIG. 15 is from the lumbar spine signal of subject 8.

Although the time locations in the first three D8 doublets of FIG. 2 were lost in the process to retrieve the $\rho$-wave of D8 doublet 4, as shown in FIG. 3, the one or more expert rules recovered and found the Pareto time-localization of the other D8 doublets at each predefined delay. With the predefined values used to exemplify the waveform matching technique ($\theta_0$=0, $\theta_1$=5, $\theta_2$=10, and $\theta_3$=15 ms), the delays $\theta_1=5$ ms for D8 doublet 1', $\theta_0=0$ ms for D8 doublet 2, $\theta_1=5$ ms for D8 doublet 3', and $\theta_3=15$ ms for D8 doublet 4''' have been found by the one or more expert rules to be on the Pareto front (see FIGS. 6A-6D).

Figure 7B:
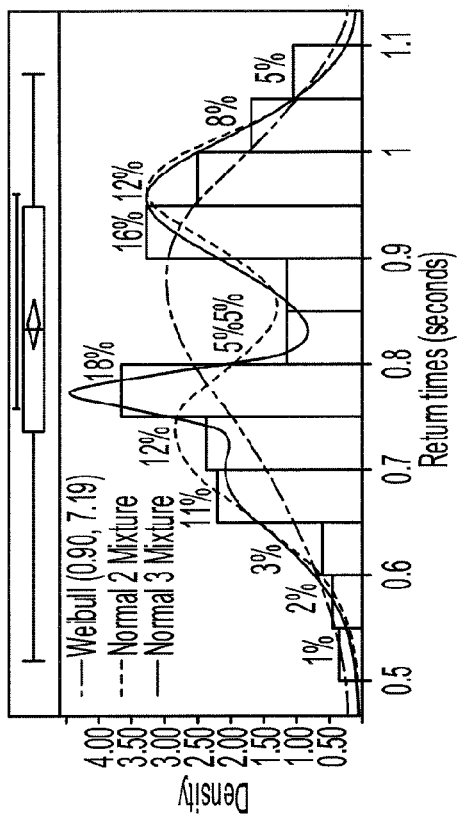
FIGS. 7A-7D illustrate distribution fitting of return times among healthy subjects according to an aspect of the invention.
Figure 7A:
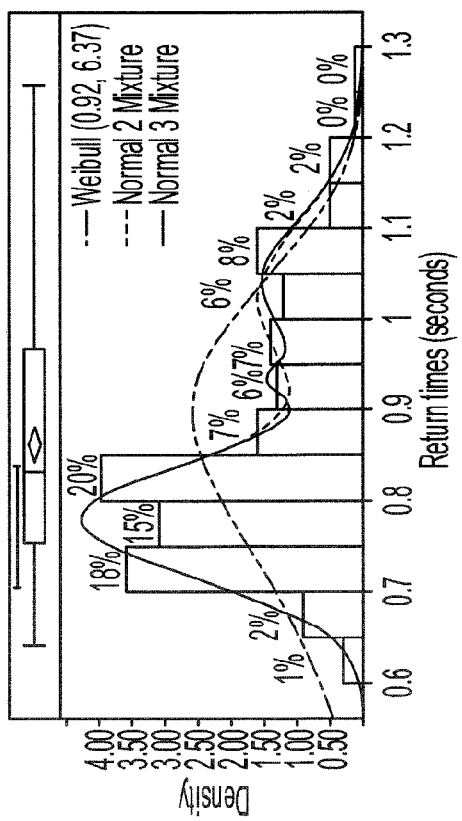
Figure 7D:
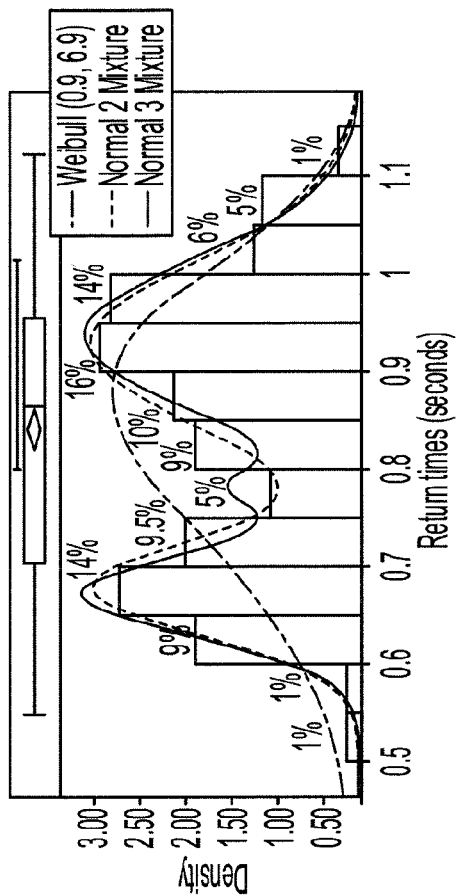
Figure 7C:
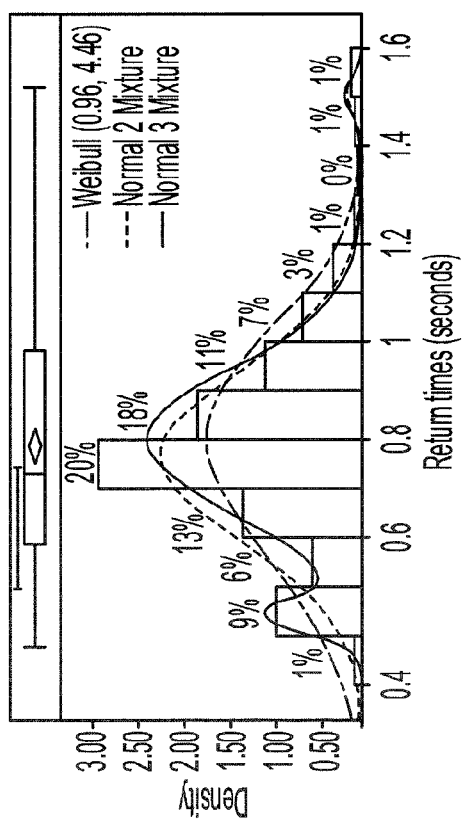
Figure 8B:
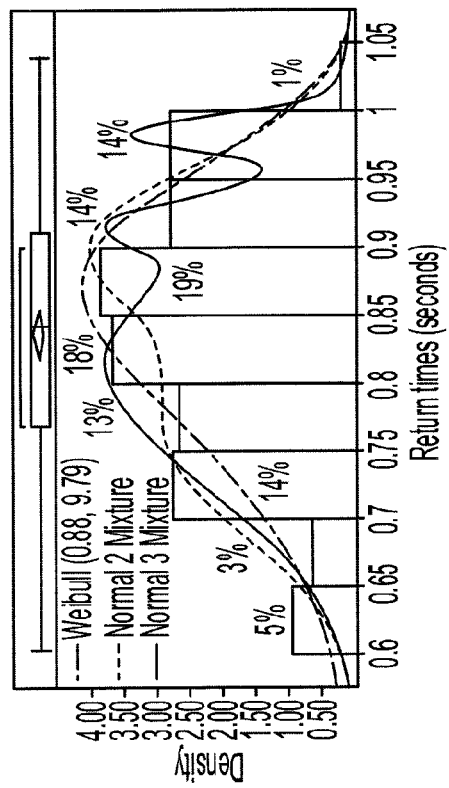
FIGS. 8A-8B illustrate distribution fitting of return times among subjects with quadriplegia according to an aspect of the invention.
Figure 8A:
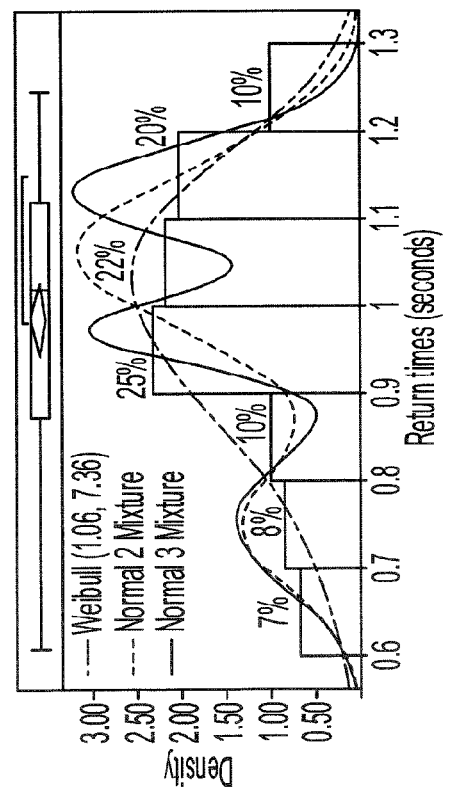

Among all the paraspinal signals, the Weibull distribution was found to be the best probability fit in the AICc sense among the quadriplegic subjects as shown in FIGS. 8A-8B; whereas the Normal 2 & 3 Mixtures were prevalently the best fit among control subjects as shown in FIGS. 7A-7D. The parameter estimates for the best-fitted distributions are reported in FIGS. 9A-9C, 10A-10C, and 11A-11C.

FIGS. 7A-7D show the probability distribution fitting of return times from healthy subjects. FIG. 7A shows the probability distribution fitting of return times from the lumbar spine signal of subject 6 with Normal 2 Mixture (AICc=−272.53), Normal 3 Mixture (AICc=−265.98), and Weibull (AICc=−199.41). FIG. 7B shows the probability distribution fitting of return times from the sacral signal of subject 8 with Normal 3 Mixture (AICc=−187.61), Normal 2 Mixture (AICc=−186.31), and Weibull (AICc=−167.78).

FIG. 7C shows the probability distribution fitting of return times from the cervical signal of subject 5 with Normal 3 Mixture (AICc=−95.26), Normal 2 Mixture (AICc=−87.19), and Weibull (AICc=−51.56). FIG. 7D shows the probability distribution fitting of return times from the cervical signal of subject 5 with Normal 3 Mixture (AICc=−95.26), Normal 2 Mixture (AICc=−87.19), and Weibull (AICc=−194.86). Lower AICc values indicate a better distribution fit.

FIGS. 8A-8B show the probability distribution fitting of return times from patients with quadriplegia. FIG. 8A shows the probability distribution fitting of return times from the thoracic signal of subject 2 with Weibull (AICc=−45.69), Normal 2 Mixture (AICc=−41.36), and Normal 3 Mixture (AICc=−35.46). FIG. 8B shows the probability distribution fitting of return times from the lumbar spine signal of subject 1 with Weibull (AICc=−231.43), Normal 2 Mixture (AICc=−227.36), and Normal 3 Mixture (AICc=−227.12). Lower AICc values indicate a better distribution fit.

The contrasting difference in the results between quadriplegic and control patients, namely in their probability distributions of D8 doublet return times and sample sizes, may point to D8 doublets becoming more prevalent (and with multimodal return times) in healthy neuromuscular systems than unhealthy ones. Furthermore, the more predominant rhythmic synchronization of neurophysiological activity of healthy subjects is consistent with the hypothesis that coherence at a distance is an indication of the nervous system able to coordinate the activity of many muscles.

It is hypothesized that the rhythmic bursts may represent a synchronization of multiple MUs firing exceptional doublets, and that there is a probable connection between them and the dynamical system theory of the return time of rare events, the Generalized Extreme Value (GEV) theory of such rare events and the neurophysiological studies by Piotrkiewicz. In the last-mentioned studies, double-firing motor units classified as single, repetitive, and exceptional doublets, constituted a small percentage (9.5%) of recorded neuronal discharges and were considered as "unusual" discharges, whereas the exceptional type was even more unusual (~1%).

In this CPG entrainment technique those D8 doublets deemed exceptional can be reproduced at will, in contrast to the studies by Piotrkiewicz, where the volunteers were not entrained to evoke doublets. In regard to the morphology of the D8 doublets, the κ and τ waves may be the result of a first and a second motor unit firing, respectively, whereas the κρσ-complex may be the result arising from some superposition between multiple first and second motor unit firings.

Similar to the normal resting heart rate between 60 and 100 beats per minute, here the observed D8 doublet return time rate is between 60 and 80 cycles per minute on average. This suggests a potential connection between HRV and BRV. The connection may be due to the ECG R-wave triggering the D8 bursts, but the physiological pathways are still unclear. However, the sEMG bursting is not a cardiac artifact for the following main reasons. First, the D8 doublets, observed during entrainment, are absent during muscle relaxation, mild voluntary contractions of the trunk or any attempt to fake the undulatory motion. Second, cardiac artifacts could manifest themselves at the thoracic level, but D8 doublets were found in the back muscles at the neck and sacral levels where cardiac artifacts are less likely. Third, the parameters of the various waves and sub-waves of D8 doublet and cardiac cycle are inconsistent as shown in the below in table.

| ECG/sEMG | ECG | sEMG |
| --- | --- | --- |
| PQRST/πκρστ | 510 ± 60 ms | ~130 ms |
| QRS/κρσ | 100 ± 20 ms | ~60 ms |
| Return time rate | 60-100/min | 60-88/min |

Besides the differences between the cardiac cycle and the D8 doublets in the above table, it is worth adding that the variability does not appear to occur within the D8 doublet but rather in its return time, as the πκρστ wave duration of ~130 ms appears to be prevailingly fixed among D8 doublets. This is unlike HRV, where a considerable amount of variability occurs among waves within same cardiac cycles. To further exemplify the difference between a pure ECG trace and the πκρστ wave found here in the sEMG traces, studies show that the return time distributions of R-waves in ECG recordings have been found Erlang in normal subjects, and a weighted average of Erlang with a second distribution (e.g. Weibull) in patients with arrhythmia. It should be noted that sEMG bursts have been observed between two consecutive ECG waves which rules out the possible ECG artifact of the sEMG bursts.

For biofeedback applications, the objective may be to help quadriplegic patients recover some motor control by learning how to evoke more D8 doublet oscillations with return time distribution deviating from Weibull (unimodal) towards normal mixtures (multimodal). Another objective may be to conduct on-line assessments by means of implementing the complete off-line technique with real-time DWT. For real-time muscle performance evaluations, it may reinforce the entrainment and training process to help increase the number of synchronized motor units, resulting in higher motor coordination and stronger muscle contractions.

The proposed technique is not restricted to only paraspinal muscles as it may span the evaluation of the neuromuscular system to a greater extent, for instance, to assess rhythmic involuntary contractions such as tremors, seizures, epilepsy, Parkinson's disease, involuntary motor disorders, or uterine contractions in pregnancy. In the former, it could provide feedback to therapies in the field. In the latter, it would monitor the return times of uterine EMG bursts to potentially warn for signs of imminent, false, or preterm labor. The proposed technique may also be applied to cardiomyocytes engineering. For example, the observed phenomenon may be interpreted as the spinal stem cells differentiating into cardiomyocytes. This may be exemplified by the sEMG bursts resembling the QRS complex of the ECG wave.

One of the major contributions is the identification of a new neurophysiological phenomenon, the Bursting Rate Variability (BRV) that bears some resemblance to Heart Rate Variability, but that still differs from it in several respects. BRV may be based on recursively shifting the Daubechies 3 wavelet transform of the raw electromyographic signal to successively provide the characterization and time-localization of spiking events by increasing the waveform matching of the raw signal and its 8-level subsignal, here referred to as "D8 doublets" due to the two adjacent and relatively high detail coefficients that span the entire rhythmic spiking phenomenon.

The presence of such D8 doublets in the sEMG signal has been conjectured to reveal coordination of muscle masses at a distance to achieve a higher hierarchy level movement. The return time statistic of the D8 doublets developed here adds some quantitative insights to this observation, with Weibull to normal mixture distribution a possible indication of a quadriplegic subject recovering some motor control.

Cardiology applications and a plausible connection with sEMG remain to be assessed by including simultaneous electrocardiogram monitoring to our sEMG protocol. Finally, from a theoretical viewpoint, it may be related to the statistic of return time of a dynamical system to some subset of its state space. The more recent Generalized Extreme Value (GEV) theory, which proceeds from the statistic of the extreme value of an observable (e.g., a sEMG signal) rather than the return time of such events, could offer an alternative way to look at the same phenomenon.

Figure 16:
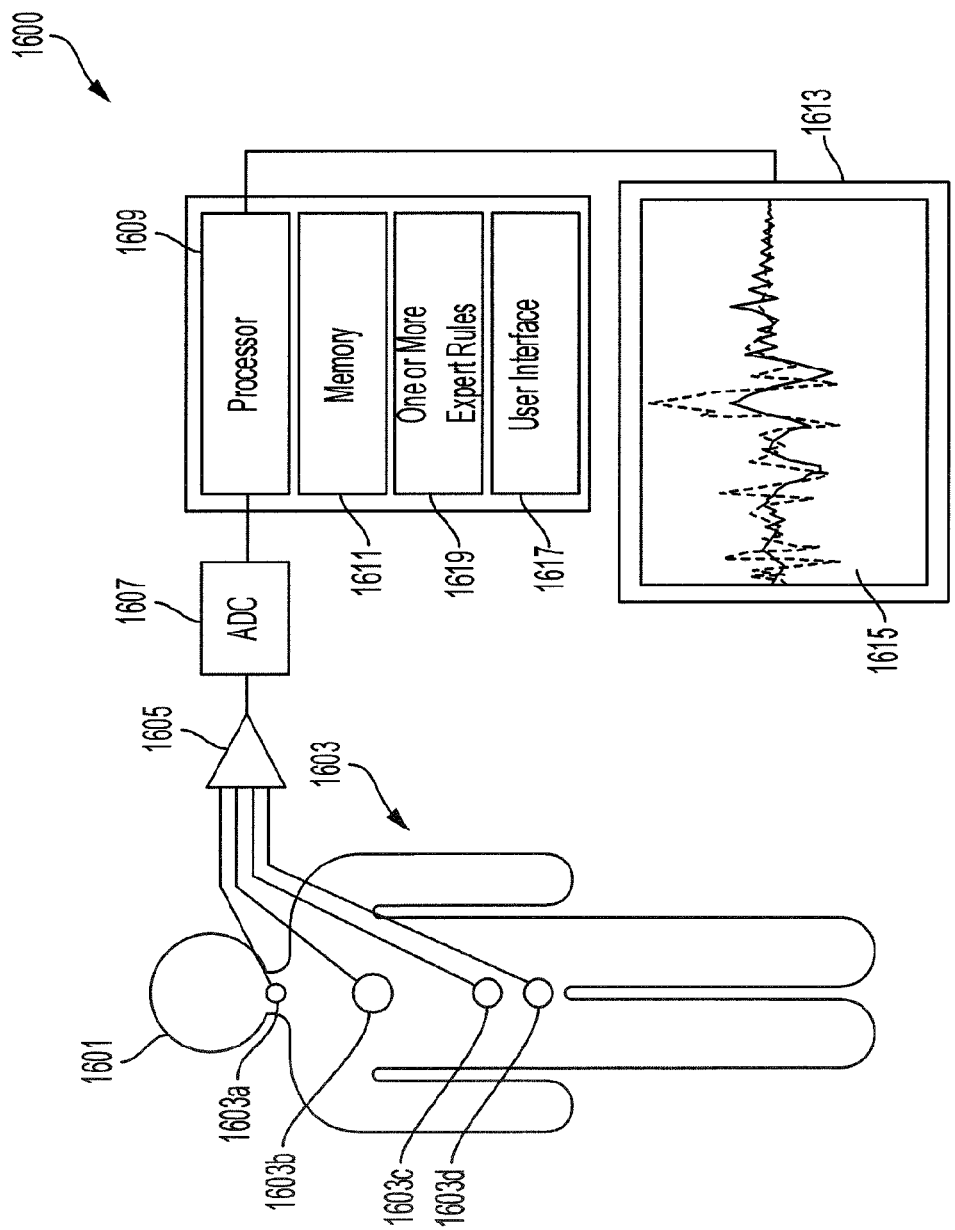
FIG. 16 illustrates a system for detecting rhythmic synchronization of motor neurons according to an aspect of the invention.

FIG. 16 shows a system 1600 for detecting rhythmic synchronization of motor neurons. The system 1600 includes one or more sensors 1603 for receiving a first signal that measures an electrical signal of one or more neurons. The one or more sensors 1603 may include one or more electrodes that are positioned on paraspinal muscles of a human 1601. In some embodiments, the first signal may be a raw signal of an electromyographic (sEMG) signal. In other embodiments, the first signal may be a raw signal of at least one of an electromyogram, an electroencephalogram, or an electrocardiogram. The one or more sensors may include one or more electrodes that are positioned on the V-points on the chest of the human 1601. The one or more sensors may include one or more electrodes that are positioned on the scalp of the human 1601 or intracortical to the human 1601. The first signal may have a first plurality of specific bursts. For example, the first signal may have four specific bursts. Additionally, each specific burst within the first plurality of specific bursts may have a temporally corresponding specific burst within the second plurality of specific bursts. For example, a third specific burst of the first signal may correspond, temporally, with a third specific burst of the second signal.

The one or more sensors 1603 may include one or more electrodes that are positioned at a cervical region 1603a of the human 1601. For example, the one or more electrodes may be positioned adjacent to the C2-C3 cervical vertebrae. The one or more sensors 1603 may include one or more electrodes that are positioned at a thoracic region 1603b of the human 1601. For example, the one or more electrodes may be positioned adjacent to the T4-T6 thoracic vertebrae. The one or more sensors may include one or more electrodes that are positioned at a lumbar region 1603c of the human 1601. For example, the one or more electrodes may be positioned adjacent to the L3 lumbar vertebrae. The one or more sensors may include one or more electrodes that are positioned at a sacral region 1603d of the human 1601. For example, the one or more electrodes may be positioned adjacent to the S2-S4 sacral vertebrae.

The system 1600 includes a processor 1609 connected to the one or more sensors 1603. The processor 1609 may be configured to receive the first signal. The system 1600 may include an amplifier 1605 to amplify the first signal prior to inputting into the processor 1609. The amplifier 1605 may have a certain bandwidth such that if the noise frequency is outside the bandwidth of the amplifier, the amplifier may reduce the noise. The system 1600 may include an analog-to-digital converter (ADC) to sample the first signal and convert the first signal into a digital signal for input into the processor 1609.

The processor 1609 may be configured to generate a second signal based on the first signal using a discrete wavelet transform. The discrete wavelet transform may be a doublet waveform that is in a D8 subband of the Daubechies 3 (db3) wavelet decomposition of the sEMG signal.

The second signal may have a second plurality of specific bursts. The second signal may have the same number of specific bursts as the first signal. For example, the second signal may have four specific bursts. According to various embodiments, the first signal may include a first plurality of peaks, a first plurality of valleys, and a first plurality of slopes between each of the peaks and valleys. The first plurality of specific bursts may be the first plurality of peaks. For example, each of the four specific bursts within the first plurality of specific bursts, as discussed above, is represented by a peak within the first plurality of peaks.

According to various embodiments, the second signal may include a second plurality of peaks, a second plurality of valleys, and a second plurality of slopes between each of the peaks and valleys. The second plurality of specific bursts may be the second plurality of peaks. For example, each of the four specific bursts within the second plurality of specific bursts, as discussed above, is represented by a peak within the second plurality of peaks.

The processor 1609 may be configured to determine a time delay between a specific burst within the first plurality of specific bursts and a specific burst within the second plurality of specific bursts using one or more expert rules 1619. For example, the processor 1609 may determine a time delay between the first specific burst (of the four specific bursts) within the first signal and the first specific burst (of the four specific bursts) within the second signal.

The time delay may be based one or more predetermined time delays inputted by a user. For example, the one or more predetermined values may be at least one of 0 ms, 5 ms, 10 ms, or 15 ms. However, other one or more predetermined time delays may be used interchangeably according to various embodiments. The one or more predetermined time delays may correspond to an omission of one or more samples. For example, the predetermined time delay of 5 ms may correspond to omission the first 20 samples, the predetermined time delay of 10 ms may correspond to an omission of the first 40 samples, and the predetermined time delay of 15 ms may correspond to an omission of the first 60 samples. In some embodiments, the one or more expert rules 1619 may determine the time delay corresponding to a minimal error between the first specific burst and the second specific burst.

The system may include a display 1613 for rendering an image 1615 that displays the first signal and the second signal. The image 1615 may display the first plurality of specific bursts and the second plurality of specific bursts. In other embodiments, the image 1615 may only display a portion of the first plurality of specific bursts and a portion of the second plurality of specific bursts. For example, the image 1615 may display only the third (of the four specific bursts) within the first plurality of specific bursts and only the third (of the four specific bursts) within the second plurality of specific bursts.

The time delay between a specific burst within the first plurality of specific bursts and a specific burst within the second plurality of specific bursts may be a temporal distance between the associated specific bursts on the display 1613. In some embodiments, the minimal error may be the shortest temporal distance between an identified specific burst within the first plurality of specific bursts and an identified specific burst within the second plurality of specific bursts.

The display 1613 may show the corresponding plurality of peaks, valleys, and slopes between each of the peaks and valleys for both the first signal and the second signal as a function of time. According to various embodiments, determining the time delay may include comparing at least one peak within the first plurality of peaks, at least one valley within the first plurality of valleys, or at least one slope within the first plurality of slopes to at least one peak within the second plurality of peaks, at least one valley within the second plurality of valleys, or at least one slops within the second plurality of slopes. The time delay may be the temporal distance between the associated at least one peak, at least one valley, or at least one slope of the respective first signal and second signal.

The system 1600 may include a memory 1611 for storing instructions for the processor 1609 to execute. The instructions may include the discrete wavelet transform. In some embodiments, the one or more expert rules 1619 may be stored in the memory 1611. In some embodiments, the memory 1611 may store the one or more predetermined time delays. The memory 1611 may include one or more of a RAM or other volatile or non-volatile memory. The memory 1611 may be a non-transitory memory or a data storage device, such as a hard disk drive, a solid-state disk drive, a hybrid disk drive, or other appropriate data storage, and may further store machine-readable instructions, which may be loaded and executed by the processor 1609.

The system 1600 may include, interface and/or interact with a user interface 1617. The user interface 1617 may include any device capable of receiving user input, such as a button, a dial, a microphone, a graphical user interface or a touch screen, and any device capable of output, e.g., a display, a speaker, or a refreshable braille display. The user interface 1617 allows a user to communicate with the processor 1609 and/or memory 1611. For example, the user may utilize the user interface 1617 to input the one or more predetermined time delays into the memory 1611.

The processor 1609 may be configured to apply the time delay to the first signal. The time delay may be applied to the first signal before the new second signal is generated by the processor 1609. For example, the processor 1609 may determine a time delay between a specific burst of the first signal and a specific burst of the second signal, apply the time delay to the first signal, and generate a new second signal based on the first signal and the applied time delay using the discrete wavelet transform. In some embodiments, the processor 1609 may apply only non-zero time delays to the first signal (e.g. 5 ms, 10 ms, 15 ms). In other embodiments, the processor 1609 may apply all time delays to the first signal (e.g. 0 ms, 5 ms, 10 ms, 15 ms).

The processor 1609 may generate the new second signal having an adjusted second plurality of specific bursts based on the first signal and the applied time delay using the discrete wavelet transform. According to various embodiments, the adjusted second plurality of specific bursts may be the second plurality of specific bursts with a specific burst within the second plurality of specific bursts adjusted by the above applied time delay. For example, if a time delay is determined between a first specific burst of the first and second signal then a generated new second signal will have the same second plurality of specific bursts as the second signal except the first specific burst within the adjusted second plurality of specific bursts will be adjusted by the above determined time delay. That is, only the first specific burst within the adjusted second plurality of specific bursts will be adjusted, all other bursts within the adjusted second plurality of specific bursts will remain the same as the ones in the second plurality of specific bursts.

The processor 1609 may be configured to determine a second time delay between a second specific burst within the first plurality of specific bursts and a second specific burst within the second plurality of specific bursts using the one or more expert rules 1619. For example, if the first time delay was determined between the first specific bursts (of the four specific bursts) between the first and second signal then the second time delay may be determined between the third specific bursts (of the four specific bursts) between the first and second signal.

The processor 1609 may be configured to apply the second time delay to the first signal. The second time delay may be applied to the first signal before the second new second signal is generated by the processor 1609 but after the first new second signal is generated by the processor 1609. For example, the processor 1609 may determine a second time delay between a second specific burst of the first signal and a second specific burst of the first new second signal, apply the second time delay to the first signal, and generate a second new second signal based on the first signal using the discrete wavelet transform. The processor 1609 may apply the first time delay and the second time delay sequentially or all at once to the first signal.

The processor 1609 may be configured to determine d-number of time delays between a d-number of specific bursts within the first plurality of specific bursts and an d-number of specific bursts within the second plurality of specific bursts. For example, the processor 1609 may determine four time delays when there are four specific bursts within the first plurality of specific bursts and four specific bursts within the second plurality of specific bursts.

The processor 1609 may be configured to apply d-number of time delays to the first signal. For example, if there are a total of four time delays determined by the processor 1609, the processor 1609 may apply four time delays to the first signal. The time delays may be applied to the first signal sequentially by the processor 1609. For example, a first time delay may be applied to the first signal, a new second signal based on the first signal is generated, a second time delay may be applied to the first signal, a second new second signal based on the first signal is generated, a third time delay may be applied to the first signal, and a third new second signal based on the first signal is generated. In other embodiments, the time delays may be applied all at once. For example, a first time delay, a second time delay, and a third time delay is applied to the first signal, and a new second signal based on the first signal is generated.

Figure 17:
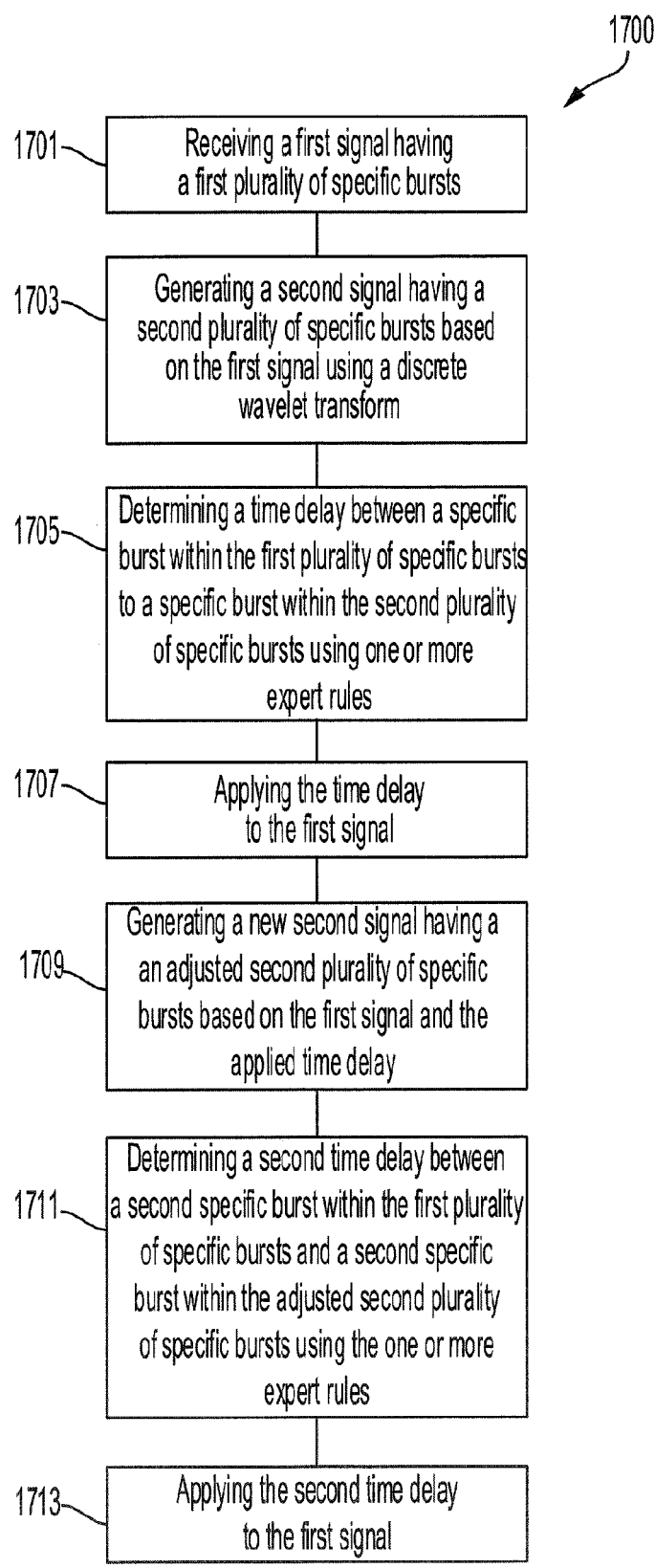
FIG. 17 illustrates a flow diagram of a process for detecting rhythmic synchronization of motor neurons according to an aspect of the invention.

FIG. 17 is a flow diagram of a process 1700 for detecting rhythmic synchronization of motor neurons.

A processor (e.g. processor 1609) may receive a first signal having a first plurality of specific bursts (1701). The number of bursts within the first plurality of specific bursts may be discrete. For example, the first signal may have four specific bursts. The first signal may be an electrical signal from one or more neurons within paraspinal muscles of a human. In some embodiments, the first signal may be a raw signal of an electromyographic (sEMG) signal. In other embodiments, the first signal may be a raw signal of at least one of an electromyogram, an electroencephalogram, or an electrocardiogram. The one or more sensors may include one or more electrodes that are positioned on the V-points on the chest of a human. The one or more sensors may include one or more electrodes that are positioned on the scalp of a human or intracortical to the human.

The processor may generate a second signal having a second plurality of specific bursts based on the first signal using a discrete wavelet transform (1703). The discrete wavelet transform may be a doublet waveform that is in a D8 subband of the Daubechies 3 (db3) wavelet decomposition of the sEMG signal. The number of bursts within the second plurality of specific bursts may be discrete and may be the same number of specific bursts as the first signal. For example, the second signal may have four specific bursts. Additionally, each specific burst within the first plurality of specific bursts may have a temporally corresponding specific burst within the second plurality of specific bursts. For example, a third specific burst of the first signal may correspond, temporally, with a third specific burst of the second signal.

According to various embodiments, the first signal may include a first plurality of peaks, a first plurality of valleys, and a first plurality of slopes between each of the peaks and valleys. The first plurality of specific bursts may be the first plurality of peaks. For example, each of the four specific bursts within the first plurality of specific bursts, as discussed above, is represented by a peak within the first plurality of peaks.

According to various embodiments, the second signal may include a second plurality of peaks, a second plurality of valleys, and a second plurality of slopes between each of the peaks and valleys. The second plurality of specific bursts may be the second plurality of peaks. For example, each of the four specific bursts within the second plurality of specific bursts, as discussed above, is represented by a peak within the second plurality of peaks.

The processor may determine a time delay between a specific burst within the first plurality of specific bursts and a specific burst within the second plurality of specific bursts using one or more expert rules (e.g. one or more expert rules 1619) (1705). For example, the processor may determine a time delay between the second specific burst (of the four specific bursts) within the first signal and the second specific burst (of the four specific bursts) within the second signal.

The time delay may be based one or more predetermined time delays inputted by a user. For example, the one or more predetermined time delays may be at least one of 0 ms, 5 ms, 10 ms, or 15 ms. However, other one or more predetermined time delays may be used interchangeably according to various embodiments. The one or more predetermined time delays may correspond to an omission of one or more samples. For example, the predetermined time delay of 5 ms may correspond to omission the first 20 samples, the predetermined time delay of 10 ms may correspond to an omission of the first 40 samples, and the predetermined time delay of 15 ms may correspond to an omission of the first 60 samples. In some embodiments, the one or more expert rules may determine the time delay corresponding to a minimal error between the first specific burst and the second specific burst.

The time delay between a specific burst within the first plurality of specific bursts and a specific burst within the second plurality of specific bursts may be a temporal distance between the associated specific bursts. In some embodiments, the minimal error may be the shortest temporal distance between an identified specific burst within the first plurality of specific bursts and an identified specific burst within the second plurality of specific bursts.

According to various embodiments, determining the time delay may include comparing at least one peak within the first plurality of peaks, at least one valley within the first plurality of valleys, or at least one slope within the first plurality of slopes to at least one peak within the second plurality of peaks, at least one valley within the second plurality of valleys, or at least one slopes within the second plurality of slopes. The time delay may be the temporal distance between the associated at least one peak, at least one valley, or at least one slope of the respective first signal and second signal.

The processor may apply the time delay to the first signal (1707). In some embodiments, the processor may apply only non-zero time delays to the first signal (e.g. 5 ms, 10 ms, 15 ms). In other embodiments, the processor may apply all time delay to the first signal (e.g. 0 ms, 5 ms, 10 ms, 15 ms).

The processor may generate a new second signal having an adjusted second plurality of specific bursts based on the first signal and the applied time delay using the discrete wavelet transform (1709). According to various embodiments, the adjusted second plurality of specific bursts may be the second plurality of specific bursts with a specific burst within the second plurality of specific bursts adjusted by the above applied time delay. For example, if a time delay is determined between a first specific burst of the first and second signal then a generated new second signal will have the same second plurality of specific bursts as the second signal except the first specific burst within the adjusted second plurality of specific bursts will be adjusted by the above determined time delay. That is, only the first specific burst within the adjusted second plurality of specific bursts will be adjusted, all other bursts within the adjusted second plurality of specific bursts will remain the same as the ones in the second plurality of specific bursts.

The processor may determine a second time delay between a second specific burst within the first plurality of specific bursts and a second specific burst within the adjusted second plurality of specific bursts using the one or more expert rules (1711). For example, if the first time delay was determined between the first specific bursts (of the four specific bursts) between the first and second signal then the second time delay may be determined between the third specific bursts (of the four specific bursts) between the first and second signal.

The processor may apply the second time delay to the first signal (1713). The second time delay may be applied to the first signal before the second new second signal is generated by the processor but after the first new second signal is generated by the processor. For example, the processor may determine a second time delay between a second specific burst of the first signal and a second specific burst of the first new second signal, apply the second time delay to the first signal, and generate a second new second signal based on the first signal and the second time delay using the discrete wavelet transform. The processor may apply the first time delay and the second time delay sequentially or all at once to the first signal.

The processor may be configured to determine d-number of time delays between a d-number of specific bursts within the first plurality of specific bursts and a d-number of specific bursts within the second plurality of specific bursts. For example, the processor may determine four time delays when there are four specific bursts within the first plurality of specific bursts and four specific bursts within the second plurality of specific bursts.

The processor may be configured to apply d-number of time delays to the first signal. For example, if there are a total of four time delays determined by the processor, the processor may apply four time delays to the first signal. The time delays may be applied to the first signal sequentially by the processor. For example, a first time delay may be applied to the first signal, a new second signal based on the first signal is generated, a second time delay may be applied to the first signal, a second new second signal based on the first signal is generated, a third time delay may be applied to the first signal, and a third new second signal based on the first signal is generated. In other embodiments, the time delays may be applied all at once. For example, a first time delay, a second time delay, and a third time delay is applied to the first signal, and a new second signal based on the first signal is generated.

Exemplary embodiments of the invention have been disclosed in an illustrative style. Accordingly, the terminology employed throughout should be read in a non-limiting manner. Although minor modifications to the teachings herein will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

What is claimed is:

1. A system for detecting rhythmic synchronization of motor neurons by applying a first time delay to a recorded electrical signal to modify the recorded electrical signal to correspond, with a minimum error, to a computed signal, the system comprising:
   one or more sensors each comprising an electrode attachable to a human body for sensing an electrical signal of one or more neurons of the human body, the electrical signal having a first plurality of specific bursts;
   an amplifier to amplify the electrical signal prior to inputting into a processor;
   an analog-to-digital converter (ADC) to sample the electrical signal and digitize electrical signal for input into the processor, and
   the processor connected to the ADC, wherein the processor:
      receives the electrical signal from the one or more sensors;
      records the electrical signal to generate a recorded electrical signal in an electronic memory;
      generates the computed signal from the recorded electrical signal using the discrete wavelet transform, the computed signal comprising a double waveform and having a second plurality of specific bursts,
      retrieves one or more expert rules from the electronic memory;
      determines a first time delay between a specific burst within the first plurality of specific bursts and a specific burst within the second plurality of specific bursts using the one or more expert rules,
         wherein the first time delay is based on one or more predetermined time delays, and
         wherein the first time delay corresponds to the minimal error between the first plurality of specific bursts and the second plurality of specific bursts, and
      applies the first time delay to the recorded electrical signal to generate a time delayed electrical signal having the first time delay so that a difference of the time delayed electrical signal and the computed signal have the minimal error; and
   a display for rendering an image that displays the time delayed electrical signal and the computed signal for the detecting of the rhythmic synchronization.

2. The system of claim 1, further comprising:
   the memory for storing instructions for the processor to execute, the instructions including the discrete wavelet transform and the one or more expert rules.

3. The system of claim 1, wherein the recorded electrical signal comprises a first plurality of peaks, a first plurality of valleys, and a first plurality of slopes between each of the peaks and valleys, the first plurality of specific bursts being the first plurality of peaks, wherein the computed signal comprises a second plurality of peaks, a second plurality of valleys, and a second plurality of slopes between each of the peaks and valleys, the second plurality of specific bursts being the second plurality of peaks.

4. The system of claim 3, wherein determining the time delay includes comparing at least one peak within the first plurality of peaks, at least one valley within the first plurality of valleys, and at least one slope within the first plurality of slopes to at least one peak within the second plurality of peaks, at least one valley within the second plurality of valleys, and at least one slope within the second plurality of slopes.

5. The system of claim 1, wherein the electrical signal is a raw signal of an electromyographic (sEMG) signal, wherein the discrete wavelet transform is the doublet waveform that is in the D8 subband of the Daubechies 3 (db3) wavelet decomposition of the sEMG signal.

6. The system of claim 5, wherein the one or more sensors include one or more electrodes that are positioned on paraspinal muscles of a human.

7. The system of claim 1, wherein the electrical signal is a raw signal of at least one of an electromyogram, an electroencephalogram, or an electrocardiogram.

8. The system of claim 1, wherein the processor is further configured to:
   generate a new computed signal having an adjusted second plurality of specific bursts using the discrete wavelet transform, the new computed signal being based on the recorded electrical signal and the time delay;
   determine a second time delay between a second specific burst within the first plurality of specific bursts and a second defined burst within the adjusted second plurality of specific bursts using the one or more expert rules; and
   apply the second time delay to the recorded electrical signal.

9. A method for detecting rhythmic synchronization of motor neurons by applying a first time delay to a recorded electrical signal to modify the recorded electrical signal to correspond, with a minimum error, to a computed signal, comprising:

sensing by one or more sensors each comprising an electrode attachable to a human body for sensing an electrical signal of one or more neurons of the human body, the electrical signal having a first plurality of specific bursts;

amplifying, by an amplifier, the electrical signal prior to inputting into a processor;

sampling and digitizing the electrical signal for input into the processor by an analog-to-digital converter (ADC);

receiving, by the processor connected to the ADC, the electrical signal having a first plurality of specific bursts from the one or more sensors;

recording, by the processor, the electrical signal to generate a recorded electrical signal in an electronic memory;

generating, by the processor, the computed signal from the recorded electrical signal using the discrete wavelet transform, the computed signal comprising a doublet waveform and having a second plurality of specific bursts;

retrieving, by the processor, one or more expert rules from the electronic memory;

determining, by the processor, a first time delay between a specific burst within the first plurality of specific bursts and a specific burst within the second plurality of specific bursts using the one or more expert rules; and applying, by the processor, the first time delay to the recorded electrical signal to generate a time delayed electrical signal having the first time delay so that a difference of the time delayed electrical signal and the computed signal have the minimal error, wherein the first time delay is based on one or more predetermined time delays, and wherein the time delay corresponds to the minimal error between the first plurality of specific bursts and the second plurality of specific bursts; and displaying, by a display connected to the processor and for rendering an image, the time delayed electrical signal and the computed signal for the detecting of the rhythmic synchronization.

10. The method of claim 9, wherein the recorded electrical signal comprises a first plurality of peaks, a first plurality of valleys, and a first plurality of slopes between each of the peaks and valleys, the first plurality of specific bursts being the first plurality of peaks, wherein the computed signal comprises a second plurality of peaks, a second plurality of valleys, and a second plurality of slopes between each of the peaks and valleys, the second plurality of specific bursts being the second plurality of peaks.

11. The method of claim 10, wherein determining the time delay includes comparing at least one peak within the first plurality of peaks, at least one valley within the first plurality of valleys, and at least one slope within the first plurality of slopes to at least one peak within the second plurality of peaks, at least one valley within the second plurality of valleys, and at least one slope within the second plurality of slopes.

12. The method of claim 9, wherein the electrical signal is a raw signal of an electromyographic (sEMG) signal, wherein the discrete wavelet transform is the doublet waveform that is in a D8 subband of the Daubechies 3 (db3) wavelet decomposition of the sEMG signal.

13. The method of claim 12, wherein the first signal is an electrical signal from one or more neurons within paraspinal muscles or in a spine of a human.

14. The method of claim 9, wherein the first signal is a raw signal of at least one of an electromyogram, an electroencephalogram, or an electrocardiogram.

* * * * *